(12) United States Patent
Tannous et al.

(10) Patent No.: US 11,950,817 B2
(45) Date of Patent: Apr. 9, 2024

(54) TWO-PART SCREW SYSTEMS AND METHODS FOR IMPLANTING SAME

(71) Applicant: SINNOV, LLC, Ashburn, VA (US)

(72) Inventors: Oliver Tannous, Washington, DC (US); Ehsan Jazini, Bethesda, MD (US); Karim Najjar, Redwood City, CA (US); William Fahey, Ridgewood, NJ (US)

(73) Assignee: SINNOV, LLC, Ashburn, VA (US)

( * ) Notice: Subject to any disclaimer, the term of this patent is extended or adjusted under 35 U.S.C. 154(b) by 330 days.

(21) Appl. No.: 17/145,307

(22) Filed: Jan. 9, 2021

(65) Prior Publication Data

US 2022/0265334 A1     Aug. 25, 2022

Related U.S. Application Data

(63) Continuation-in-part of application No. 15/854,533, filed on Dec. 26, 2017, now abandoned.

(60) Provisional application No. 62/439,960, filed on Dec. 29, 2016.

(51) Int. Cl.
| | |
|---|---|
| *A61B 17/86* | (2006.01) |
| *A61B 17/80* | (2006.01) |
| *A61B 17/84* | (2006.01) |

(52) U.S. Cl.
CPC ........ *A61B 17/8685* (2013.01); *A61B 17/864* (2013.01); *A61B 17/8038* (2013.01); *A61B 17/844* (2013.01); *A61B 2017/8655* (2013.01)

(58) Field of Classification Search
CPC .............. A61B 17/8685; A61B 17/864; A61B 17/8875; A61B 17/8038; A61B 17/844; A61B 17/8615; A61B 17/8605; A61B 17/8625; A61B 17/8655
USPC ....... 606/300–304, 308, 309, 314, 319, 320, 606/322, 323, 328, 329; 411/45, 46, 325, 411/383, 384, 479, 356–359, 922
See application file for complete search history.

(56) References Cited

U.S. PATENT DOCUMENTS

| | | | |
|---|---|---|---|
| 5,720,753 A | 2/1998 | Sander et al. | |
| 6,319,254 B1 | 11/2001 | Giet et al. | |
| 2007/0038221 A1* | 2/2007 | Fine ..................... | A61F 2/0811 606/232 |

(Continued)

FOREIGN PATENT DOCUMENTS

WO    WO-2017147537 A1 *   8/2017  ......... A61B 17/7225

*Primary Examiner* — Marcela I. Shirsat
(74) *Attorney, Agent, or Firm* — THE MARBURY LAW GROUP, PLLC

(57) ABSTRACT

A two-part screw system includes an inner member and a cannulated outer member that may be pre-assembled with an inner member driver and an outer member driver to form a surgical assembly. A method of inserting the two-part screw system includes advancing the inner member into the bone by using the inner member driver, and advancing the outer member into the bone by using the outer member driver. The inner member acts as a guide for the outer member, and eliminates the need for a separate guide wire. The pre-assembled nature of the surgical assembly eliminates the need to sequentially remove and apply drivers and implant parts. The inner member and the outer member are configured to integrate into a substantially solid body when in a final alignment, thus forming a stronger implant than a cannulated screw.

18 Claims, 15 Drawing Sheets

(56) References Cited

U.S. PATENT DOCUMENTS

| | | | |
|---|---|---|---|
| 2008/0161854 A1* | 7/2008 | Bae | A61B 17/7007 606/301 |
| 2009/0248089 A1 | 10/2009 | Jacofsky et al. | |
| 2010/0298892 A1 | 11/2010 | Biyani et al. | |
| 2011/0046682 A1 | 2/2011 | Stephan et al. | |
| 2011/0190821 A1 | 8/2011 | Chin et al. | |
| 2013/0211464 A1* | 8/2013 | Lin | A61B 17/8605 606/304 |
| 2013/0245697 A1 | 9/2013 | Hulliger | |
| 2015/0127056 A1 | 5/2015 | Roybal | |
| 2015/0327902 A1 | 11/2015 | Eekhoff et al. | |

\* cited by examiner

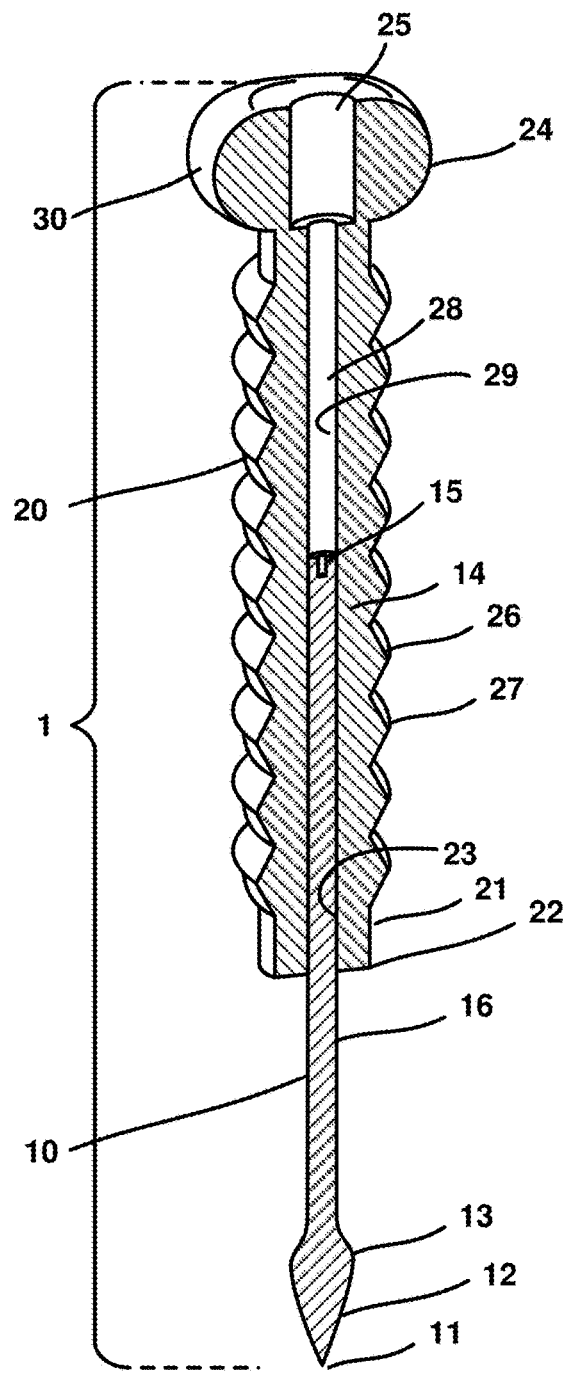
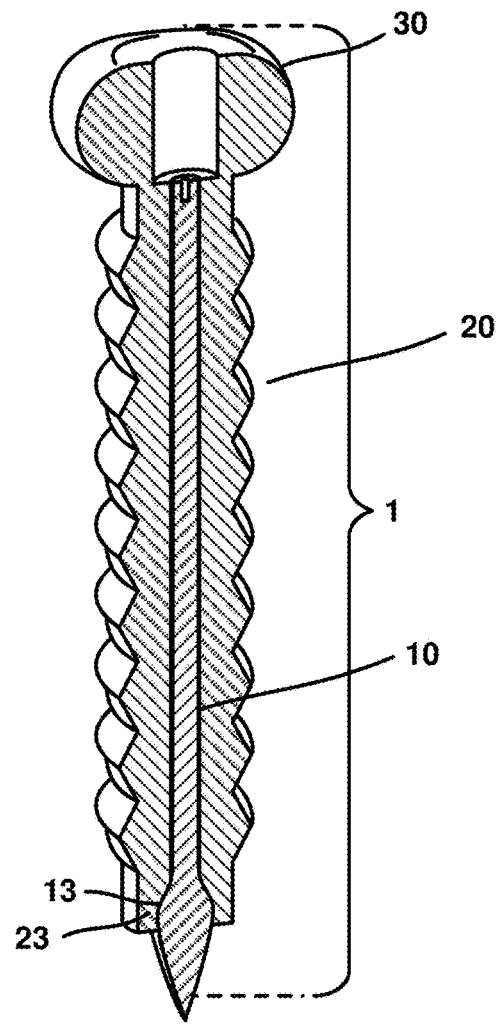
FIG. 1A
FIG. 1B

TWO-PART SCREW SYSTEMS AND METHODS FOR IMPLANTING SAME

RELATED APPLICATIONS

This application claims the benefit of priority to U.S. Provisional Patent Application No. 62/439,960 titled "Percutaneous Screw System That Eliminates the Need for a Guide Wire" filed Dec. 29, 2016 and U.S. Non-provisional patent application Ser. No. 15/854,533 titled "Percutaneous Screw Systems and Methods for Implanting the Same Without the Need for a Guide Wire" filed Dec. 26, 2017, the entire contents of both are hereby incorporated by reference for all purposes.

BACKGROUND

Certain types of orthopedic surgery involve insertion of a screw into bone, for example insertion of a pedicle screw into a pedicle of a vertebra during spinal surgery. Typical minimally invasive spinal surgery techniques include insertion of a cannulated spinal needle such as a jamshidi needle with the assistance of various imaging techniques, placement of a guide wire within the cannula of the spinal needle, removal of the spinal needle, placement of a cannulated pedicle screw over the guide wire, advancement of the cannulated pedicle screw with a driver, and removal of the guide wire and driver. This technique has numerous drawbacks attributable to the multiple steps in inserting and removing various parts, the risk that the guide wire advances beyond the vertebra and punctures the aorta or abdomen, the potential for the guide wire to form kinks and/or become bound within the screw, and/or the weaker nature of a cannulated screw. There exists a need for a screw system that eliminates the need for a guide wire, reduces the number of steps required to insert a screw, and results in a stronger implanted screw.

SUMMARY

The various aspects include a two-part screw system and methods of implanting the two-part screw system in bone. The two-part screw system includes an inner member and a cannulated outer member that may be pre-assembled with an inner member driver and an outer member driver to form a surgical assembly. The inner member is advanced into the bone by using the inner member driver, and the outer member is advanced into the bone by using the outer member driver. The inner member acts as a guide for the outer member, and eliminates the need for a separate guide wire. The pre-assembled nature of the surgical assembly eliminates the need to sequentially remove and apply drivers and implant parts. The inner member and the outer member may be configured to integrate into a substantially solid body when the inner member is fully seated or almost fully seated inside the outer member, thus forming a stronger implant than a cannulated screw.

In a further aspect, the inner member has a distal end capable of advancing into bone when force is applied to the inner member. In a further aspect, the inner member has a distal end capable of advancing into bone when axial force is applied to the inner member. In some embodiments, the inner member has a distal end with a pointed tip.

In a further aspect, the inner member has a proximal end capable of engagement with a distal end of the inner member driver. In some embodiments, the inner member and the inner member driver have an engagement that restricts relative axial movement between the inner member and the inner member driver.

In a further aspect, the outer member is capable of advancing into bone when force is applied to the outer member. In a further aspect, the outer member is capable of advancing into bone when rotational force is applied to the outer member. In some embodiments, the outer member has a distal end with a self-cutting and/or self-tapping tip. In a further aspect, the outer member has an outer surface including at least one threaded portion.

In a further aspect, the outer member has a proximal end capable of engagement with a distal end of the outer member driver. In some embodiments, the outer member and the outer member driver have an engagement that restricts relative axial movement and relative radial movement between the outer member and the outer member driver.

In a further aspect, the inner member protrudes from the outer member in the surgical assembly, such that the inner member may contact the bone before the outer member. In a further aspect, the length of inner member that protrudes from the outer member may be adjustable. In a further aspect, the length of inner member that protrudes from the outer member may be temporarily fixed. In a further aspect, the length of inner member protruding from the outer member may be determined by the relative position of the inner member driver and the outer member driver.

In a further aspect, the surgical assembly is advanced toward the bone by applying an axial force to the inner member driver. The inner member penetrates the bone. In a further aspect, the advancement of the surgical assembly toward the bone is halted by the abutment of the distal end of the outer member against the surface of the bone. In a further aspect, the outer member is advanced into the bone by applying a rotational force to the outer member driver.

In a further aspect, the outer surface of the inner member and/or the inner surface of the outer member are configured such that relative axial movement between the inner member and the outer member is not restricted until the inner member is fully seated or almost fully seated inside the outer member, in what in some embodiments is referred to as a final alignment. In a further aspect, the outer surface of the inner member and/or the inner surface of the outer member are configured such that relative radial movement between the inner member and the outer member is not restricted.

In a further aspect, the inner member and/or the outer member may include interference portions that form an interference fit between the inner member and the outer member in particular configurations. The interference fit may restrict relative axial movement between the inner member and the outer member when in a final alignment. In some embodiments, the interference fit may restrict relative radial movement between the inner member and the outer member when in a final alignment. In other embodiments, the interference fit may not restrict relative radial movement between the inner member and the outer member when in a final alignment. In yet other embodiments, an outer member interference fit portion is formed as a deformation in the cannula after the inner member is inserted therein, thereby trapping the inner member substantially within the cannula of the outer member. In some embodiments, the deformation may be a protrusion into the cannula configured to engage a proximal portion of the inner member, thereby limiting further movement of the inner member toward the proximal end of the outer member.

In a further aspect, the inner member and the outer member in final alignment may be advanced further into the bone or be withdrawn from the bone as a single unit by applying a rotational force or a counter-rotational force, respectively, to the outer member.

Further aspects may include a two-part screw having an inner member that includes an inner member distal end, an inner member proximal end, and at least one inner member interference fit portion, and an outer member that includes an outer member distal end, an outer member proximal end, a cannula, and at least one outer member interference fit portion. In some aspects, the inner member may be configured to fit within the cannula of the outer member. In some aspects, the inner member may be unrestricted in axial and/or radial movement in at least one configuration within the cannula of the outer member. In some aspects, at least one inner member interference fit portion and at least one outer member interference fit portion may be configured to form an interference fit between the inner member and the outer member when the inner member is substantially within the cannula of the outer member. In some aspects, the inner member of the two-part screw may include a tip at the inner member distal end that is suitable for advancing the screw into bone when an axial force is applied. In some aspects, the inner member may include an inner member engagement part at the inner member proximal end that is suitable for engaging with an inner member driver. In some aspects, the inner member interference fit portion may include at least one portion having a larger diameter. In some aspects, the inner member interference fit portion may be located at the inner member distal end. In some aspects, at least one of the inner member and the cannula of the outer member may be threadless. In some aspects, the outer member may include at least one threaded portion on an outer surface. In some aspects, the outer member may include a self-tapping and/or self-cutting tip at the outer member distal end. In some aspects, the outer member may include an outer member engagement part at the outer member proximal end that is suitable for engaging with an outer member driver. In some aspects, the outer member interference fit portion may be within the cannula and/or may include at least one portion having a smaller diameter. In some aspects, the outer member interference fit portion may be located at the outer member proximal end.

Further aspects may include a surgical assembly that includes a two-part screw, at least one outer member driver, and at least one inner member driver. The two-part screw may include an inner member and an outer member. The outer member may include an outer member distal end, an outer member proximal end that includes an outer member engagement part, an outer member cannula, and at least one outer member interference fit portion. The inner member may be partially within the cannula, and include an inner member a distal end, an inner member proximal end including an inner member engagement part, and at least one inner member interference fit portion. In some aspects, inner member may be unrestricted in axial and/or radial movement in at least one configuration within the cannula of the outer member, and the at least one inner member interference fit portion and the at least one outer member interference fit portion may be configured to form an interference fit between the inner member and the outer member when the inner member is substantially within the cannula of the outer member. In some aspects, at least one outer member driver may include an outer driver handle, a cannulated outer driver shaft, and an outer driver proximal end including an outer driver engagement part in fixed rotational engagement with the outer member engagement part. In some aspects, at least one inner member driver may include an inner driver handle proximal to the outer driver handle, an inner driver shaft within the cannulated outer driver shaft, and an inner driver proximal end including an inner driver engagement part in fixed axial engagement with the inner member engagement part. In some aspects, the length of the inner member protrudes from the distal end of the outer member is determined by the positions of the inner driver and the outer driver. In some aspects, the length the inner member protrudes from the distal end of the outer member may be fixed by the positions of the inner driver and the outer driver. In some aspects, the distal end of the inner member driver may be within the cannula of the outer member. In some aspects, at least the proximal portion of the inner member and at least the distal portion of the inner driver shaft may be monolithically formed.

Further aspects may include methods of implanting a bone screw, which may include assembling a surgical assembly, applying an axial force to the inner driver handle to advance the inner member into the bone and advance the surgical assembly toward the bone, applying a rotational force to the outer driver handle to advance the outer member into the bone and advance the outer member over the inner member, locking the inner member to the outer member by advancing the at least one outer interference fit portion over the at least one inner interference fit portion, removing the inner member driver, and removing the outer member driver. In some aspects, the axial force is applied to the inner member driver by striking the inner driver handle with a tool. In some aspects, the method may further include using at least one imaging technique to image the trajectory and location of the inner member before, during, and/or after applying axial force to the inner driver handle.

Further aspects may include a surgical assembly kit that includes at least one two-part screw (bone screw), at least one outer member driver, and at least one inner member driver. In some aspects, the two-part screw may include an inner member including a distal end, a proximal end including an inner member engagement part, and at least one inner member interference fit portion, and an outer member including a distal end, a proximal end including an outer member engagement part, a cannula, and at least one outer member interference fit portion, in which the inner member is configured to fit within the cannula of the outer member, in which the inner member is unrestricted in axial and/or radial movement in at least one configuration within the cannula of the outer member, and in which the at least one inner member interference fit portion and the at least one outer member interference fit portion are configured to form an interference fit between the inner member and the outer member when the inner member is substantially within the cannula of the outer member. In some aspects, at least one inner member driver may include an inner driver handle, an inner driver shaft, and an inner driver proximal end including an inner driver engagement part configured to engage the inner member engagement part. In some aspects, at least one outer member driver may include an outer driver handle, a cannulated outer driver shaft configured to accept the inner driver shaft, and an outer driver proximal end including an outer driver engagement part configured to engage the outer member engagement part. In some aspects, the outer driver handle may be configured to be distal to the inner driver handle Further aspects may include the inner member being at least partially disposed within the cannula of the outer member and configured to move axially within the cannula between a deployed position and a retracted position. The outer member interference fit portion may be configured to trap the inner member substantially within the cannula of the outer member.

Further aspects may include the cannula of the outer member being only configured to receive the inner member therein from the proximal end of the outer member. The cannula may include an inner threading in the proximal end of the outer member that does not extend to the distal end of the outer member. The inner member may include an outer threading that is configured to fit into the inner threading of the outer member. The outer member interference fit portion may be formed as a defect in the inner threading that prevents the inner member from moving any further axially toward the proximal end of the outer member once the inner member engages the defect. A portion of at least one of the inner member and/or the cannula may not include threading. In the deployed position, a distal portion of the inner member that extends from a tip at the distal end of the inner member toward the proximal end of the inner member may be disposed outside the cannula, wherein in the retracted position at least some of the distal portion is disposed inside the cannula. The proximal end of the outer member may include a pilot hole configured to receive a punch tool for forming the outer member interference fit portion after the inner member has been loaded into the outer member.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain features of the invention.

FIG. 1A is a cross-sectional view of a two-part screw in an initial alignment according to various embodiments.

FIG. 1B is a cross-sectional view of a two-part screw in a final alignment according to various embodiments.

DETAILED DESCRIPTION

Figure 2A:
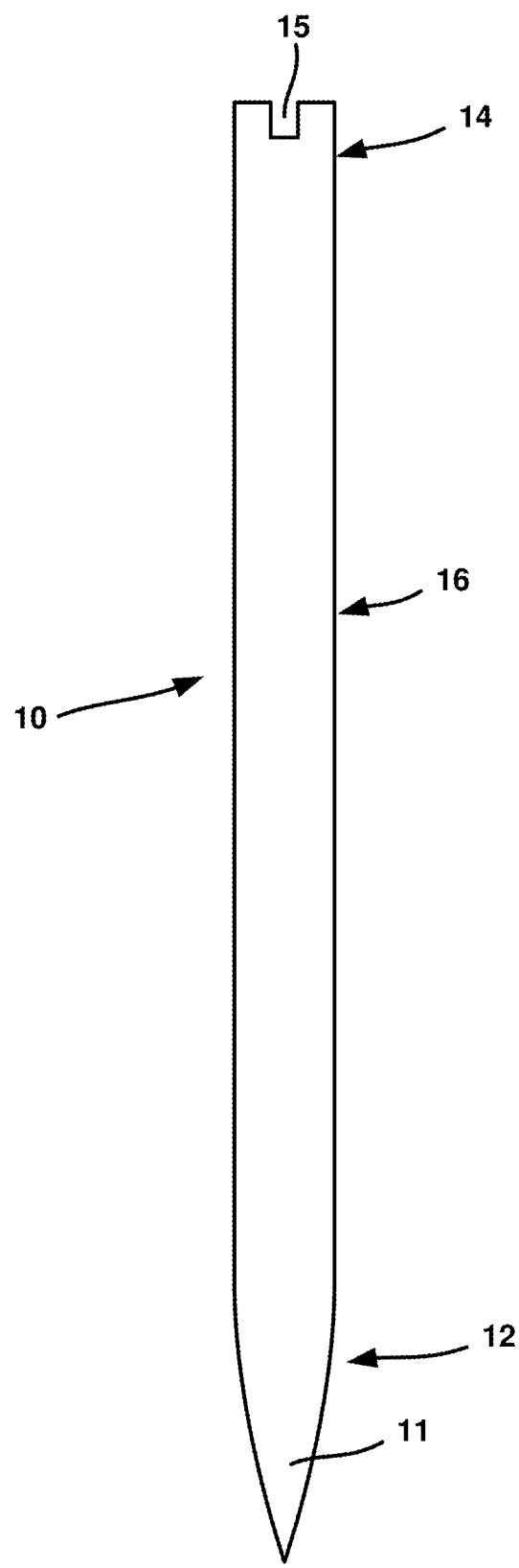
FIG. 2A is a diagram illustrating constant width inner member according to various embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The terms "screw," "pedicle screw," and "implant" may be used interchangeably herein, and may refer to any one of various devices having an elongate shaft and a head. In a preferred embodiment, a screw is a two-part pedicle screw, which is configured for implantation into a vertebral pedicle.

As used herein, the term "final alignment" refers to the final intended configuration of the two-part screw when fully implanted in a bone. In the final alignment, the inner member is inserted into the outer member as far as intended.

Existing techniques of minimally invasive orthopedic surgery typically require multiple tools and devices being inserted and withdrawn, which can increase the risk of misplacement and/or malfunctioning of the tools or devices. Furthermore, existing techniques implant cannulated screws, which are not as strong as solid screws.

Conventional attempts at solving the problem include a surgical system as described in U.S. Patent Publication No. 2015/0127056 dated May 7, 2015, the entire contents of which is hereby incorporated by reference in its entirety and for all purposes. This system includes a two-part screw that results in a solid-like implant, but such a system still requires complicated surgical steps, such as removal and introduction of various tools and implants during the surgery. For example, after implanting an inner member, the handle of the surgical instrument is removed, a cannulated outer member is placed over the inner member, and another surgical instrument is introduced to drive the cannulated outer member over the inner member. In addition, the outer surface of the inner member and the inner surface of the outer member are both threaded to allow the inner member and the outer member to be secured together when the outer member is advanced into the bone. The threaded engagement can create the potential for cross-threading, which can hinder implantation of the outer member, or even drive the inner member too far into the bone. The threaded engagement may also make it difficult to remove and/or reposition the inner member, as unscrewing the outer member from the bone could also unscrew the outer member from the inner member, thus stranding the inner member within the bone.

The various embodiments include a two-part screw, a surgical assembly, and methods of inserting the two-part screw that overcome the disadvantages of conventional minimally invasive surgical techniques and implants.

The two-part screw includes an inner member and an outer member that are coaxial and form a substantially solid implant. Relative movement of the inner member and the outer member is not restricted until the inner member and the outer member are in a final alignment, which greatly reduces the possibility that the inner member is mistakenly driven too far into the bone by the outer member. Once in final alignment, the inner member and the outer member form an interference fit that allows the inner member and outer member to be removed and/or repositioned as a single unit.

In the surgical assembly according to the invention, all tools and implants, including the inner member, outer member, inner member driver, and outer member driver, are pre-assembled before beginning the surgical procedure. In addition, the surgical assembly may be configured to prevent insertion of the inner member too far into the bone. The surgical assembly eliminates the need to remove and/or introduce tools or implants during the surgical procedure, which saves time, reduces the potential for introducing the incorrect tool or implant during the procedure, and reduces the risk of misplacement and/or malfunctioning of the implant or tools.

Two-Part Screw

FIG. 1A is a diagram illustrating a two-part screw according to various embodiments. As shown in FIG. 1A, a two-part screw 1 includes an inner member 10 and an outer member 20. The inner member 10 fits within a cannula 28 of the outer member 20. In various embodiments, when the two-part screw 1 is not in final alignment, as shown in FIG. 1A, relative axial movement between the inner member 10 and the outer member 20 is not restricted.

FIG. 1B is a diagram illustrating a two-part screw in a final alignment according to various embodiments. As shown in FIG. 1B, inner member 10 and outer member 20 are in the final alignment. In some embodiments, when the two-part screw 1 is in the final alignment, as shown in FIG. 1B, relative axial movement between the inner member 10 and the outer member 20 is restricted, prevented, or eliminated.

Inner Member

FIG. 2A is a diagram illustrating an inner member according to various embodiments. As shown in FIG. 2A, the inner member 10 has a generally elongate shape with a generally constant width, and includes an inner member distal end 12, an inner member proximal end 14, and an inner member shaft 16.

The inner member distal end 12 is configured to allow the inner member 10 to advance into bone when force is applied to the inner member 10. In some embodiments, the inner member distal end 12 may have an inner member tip 11 that is tapered, pointed and/or sharp. For example, the inner member tip 11 may include sharp conical point that is suitable for penetrating vertebra or other bone tissue.

Figure 6:
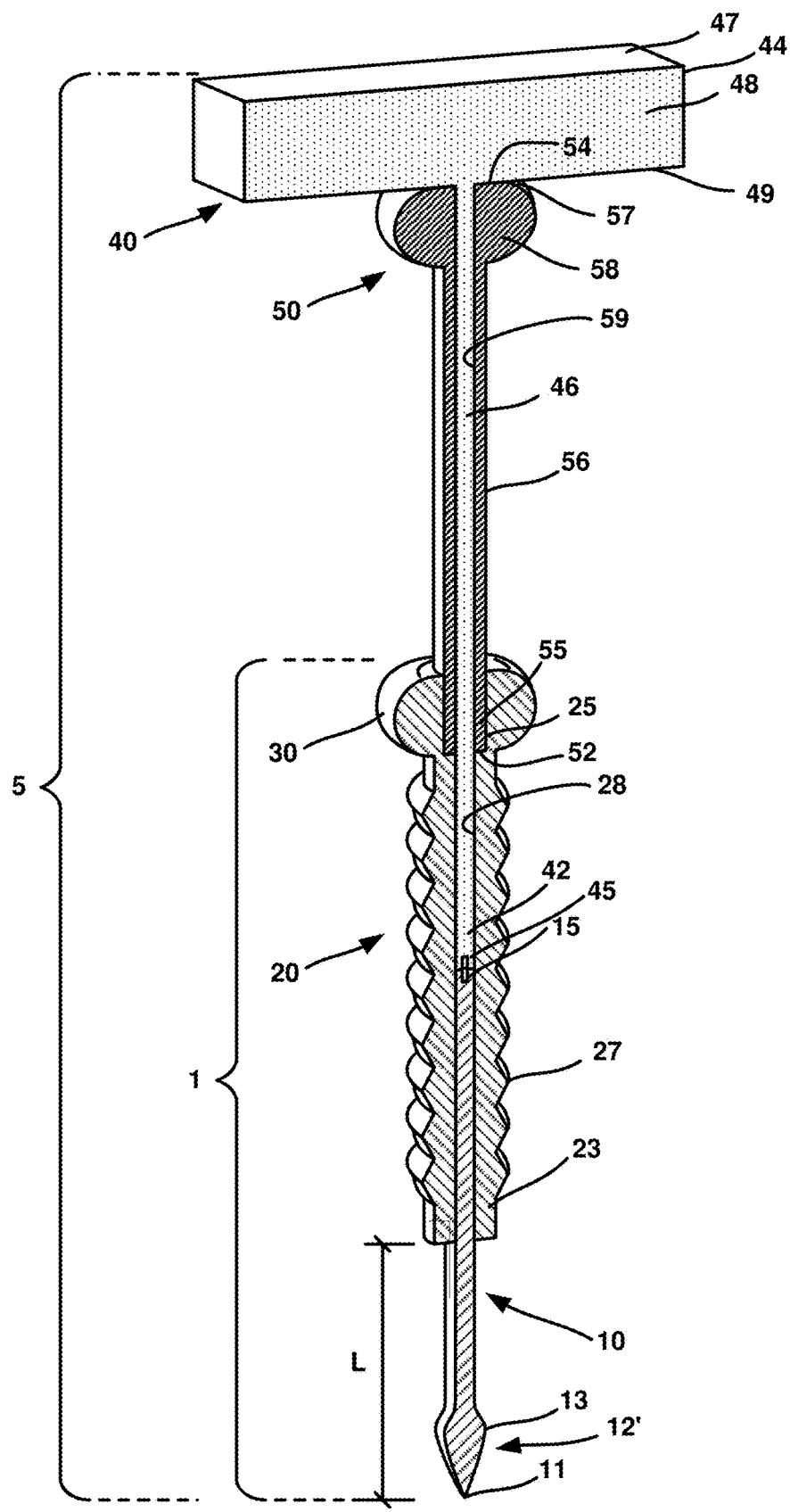
FIG. 6 is a cross-sectional view of a surgical assembly according to various embodiments.

In some embodiments, the inner member 10 includes an inner member engagement part 15 at the inner member proximal end 14. In an embodiment, the inner member engagement part 15 may be configured to engage with an inner member driver 40, as shown in FIG. 6. The engagement between the inner member engagement part 15 and the inner member driver is discussed in detail further below.

As illustrated in FIG. 2A, the inner member shaft 16 may be generally elongate in shape, with a substantially linear axis and a constant thickness (i.e., width). In some embodiments, the inner member shaft 16 may be substantially cylindrical in shape. In various embodiments, the inner member shaft 16 may have a cross section that is circular, triangular, square, rectangular, pentagonal, hexagonal, or star-shaped. According to various embodiments, the inner member shaft 16 is free of protrusions that would restrict relative axial movement and/or relative radial movement between the inner member 10 and the outer member 20 when the two-part screw 1 is not in final alignment. In exemplary embodiments, the inner member shaft 16 is threadless.

Figure 2B:
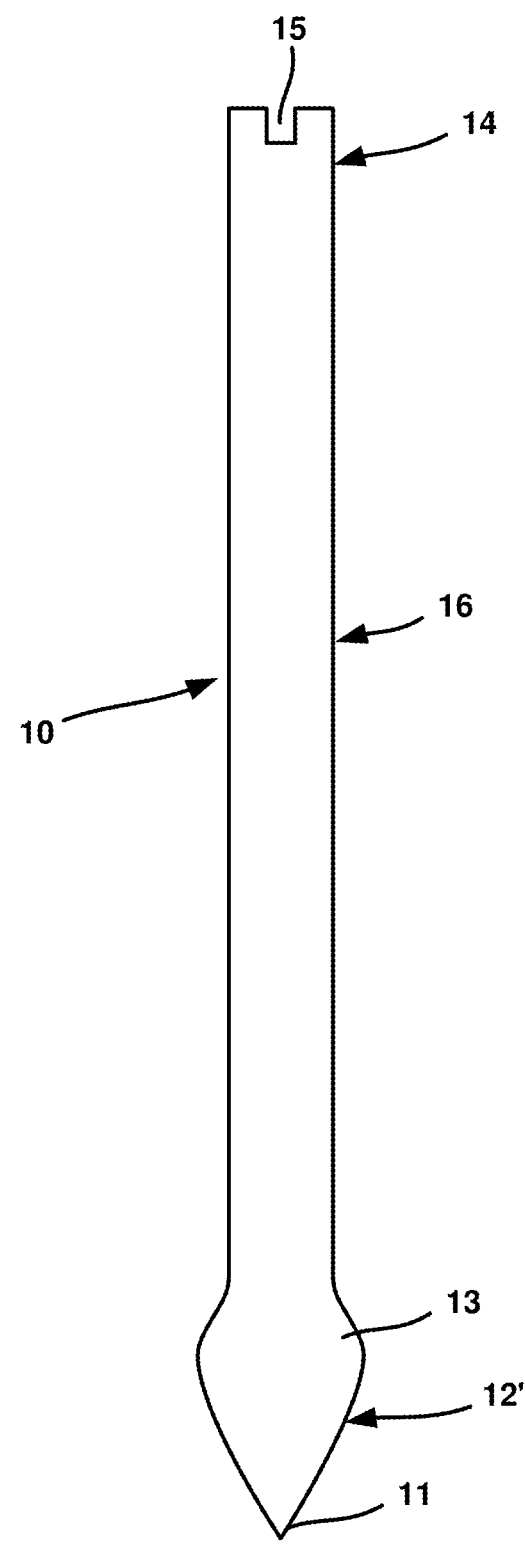
FIG. 2B is a diagram illustrating a bulged tip inner member according to various embodiments.
Figure 4:
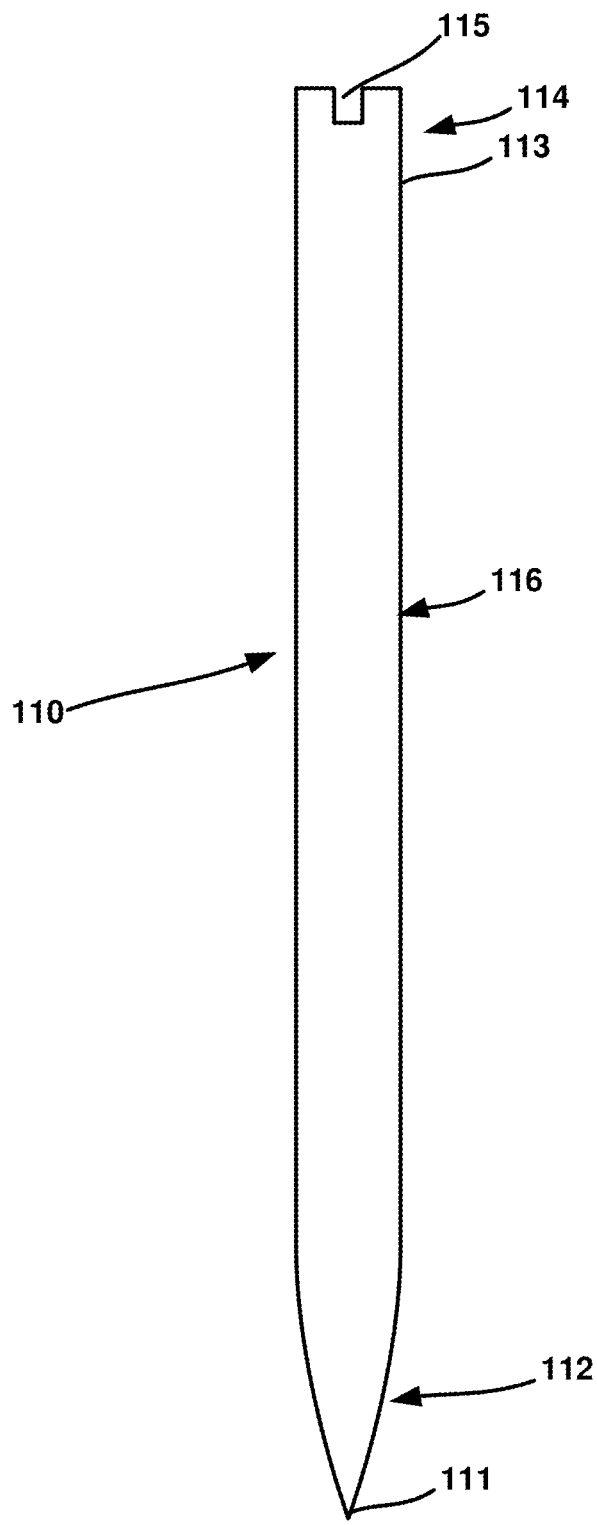
FIG. 4 is a diagram illustrating an inner member according to various embodiments.

In some embodiments, as shown in FIG. 2B, after the inner member 10 has been installed in the outer member (e.g., 20), a portion of the inner member distal end 12' may be axially compressed to create an interference fit portion 13 with a larger diameter, which is wider than the rest of the inner member 10. That interference fit portion 13 may serve as an interference fit portion for the inner member 10. In other embodiments, as shown in FIG. 4, the entire length of the inner member 110 may be consistent in diameter and remain that way after assembly with the outer member.

The dimensions of the inner member 10 is such that the inner member 10 is robust enough to advance through bone and to prevent buckling or bending when an axial force is exerted upon the inner member 10.

In some embodiments, the diameter of the inner member shaft 16 ranges from about 8 gauge to about 14 gauge, from about 9 gauge to about 12 gauge, from about 10 gauge to about 12 gauge, or from about 9 gauge to about 11 gauge. In some embodiments, the diameter of the inner member shaft 16 ranges from about 2 mm to about 4 mm, from about 2.1 mm to about 3.9 mm, from about 2.2 mm to about 3.8 mm, from about 2.3 mm to about 3.7 mm, from about 2.4 mm to about 3.6 mm, from about 2.5 mm to about 3.5 mm, from about 2.6 mm to about 3.4 mm, from about 2.7 mm to about 3.3 mm, or from about 2.8 mm to about 3.2 mm. In exemplary embodiments, the diameter of the inner member shaft 16 is about 11 gauge. In exemplary embodiments, the diameter of the inner member shaft 16 is about 3 mm.

Figure 3:
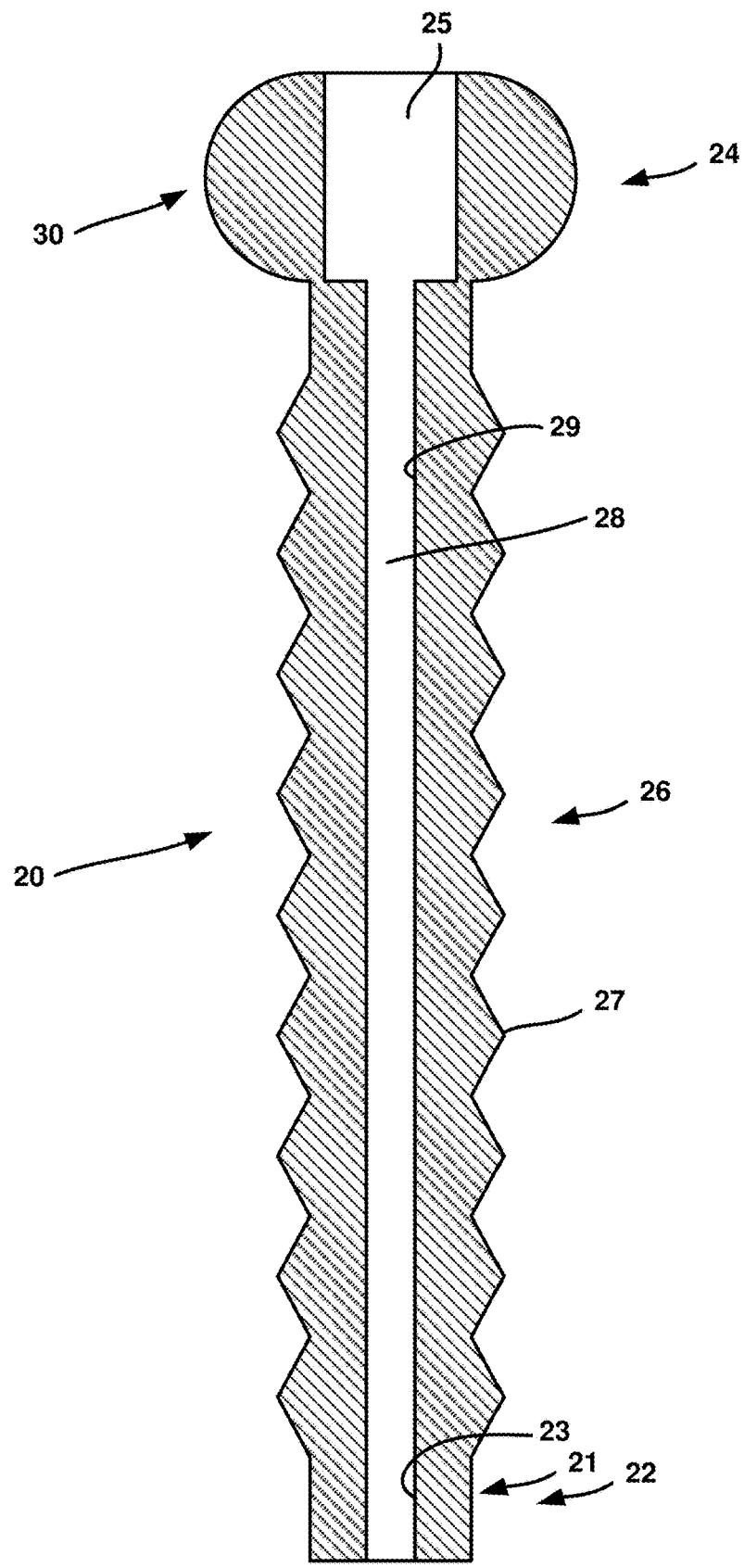
FIG. 3 is a cross-sectional view of an outer member according to various embodiments.

The inner member may be substantially the same length as the outer member shaft 26. In some embodiments, the length of the inner member 10 ranges from about 10 mm to about 70 mm, from about 15 mm to about 65 mm, from about 20 mm to about 60 mm, from about 25 mm to about 55 mm, from about 30 mm to about 55 mm or from about 35 mm to about 60 mm. In exemplary embodiments, the length of the inner member 10 is about 40 mm. In some embodiments, the length of the inner member 10 ranges from about 30 mm to about 35 mm, from about 35 mm to about 40 mm, from about 40 mm to about 45 mm, from about 45 mm to about 50 mm, from about 50 mm to about 55 mm or from about 55 mm to about 60 mm. In exemplary embodiments, the length of the inner member 10 is about 40 mm Outer Member FIG. 3 is a diagram illustrating an outer member according to various embodiments. As shown in FIG. 3, outer member 20 has a generally elongate shape, and includes an outer member distal end 22, an outer member proximal end 24, an outer member shaft 26, and an outer member cannula 28.

The outer member 20 is capable of advancing into bone when force is applied to the outer member 20. In some embodiments, the outer member 20 is capable of advancing into bone when rotational force is applied to the outer member 20. In some embodiments, the outer member shaft 26 has an outer member outer surface 27 that has at least one protrusion configured to anchor the outer member 20 into bone. In various embodiments, the outer member outer surface 27 includes at least one threaded portion for advancing the outer member 20 into bone when rotational force is applied to the outer member 20, and also for anchoring the outer member 20 into bone.

According to some embodiments, the outer member 20 includes self-cutting and/or self-tapping tip 21 at the outer member distal end 22. The self-cutting and/or self-tapping tip 21 allows the outer member 20 to advance into bone without the need for making a bore or pilot hole in the bone for receiving the two-part screw 1. In other embodiments, the outer member 20 does not include a self-cutting or self-tapping tip.

In some embodiments, the outer member 20 includes an outer member engagement part 25 at the outer member proximal end 24. In various embodiments, the outer member engagement part 25 is configured to engage with an outer member driver (e.g., 50, as shown in FIG. 6).

In some embodiments, the outer member 20 includes a head 30 at the outer member proximal end 24. In various embodiments, the head 30 may be configured to embrace, engage, clasp, grip, induce, employ, interact, or associate with other devices such as rods, plates, or cages, according to the needs of the surgery. The head 30 may be a head for a polyaxial screw or a monoaxial screw. In some embodiments, the head 30 is removable from the outer member shaft 26, and is optionally exchangeable with other heads. In other embodiments, the head 30 is not removable from the outer member shaft 26. In exemplary embodiments, the head 30 is a tulip head for receiving a rod for spinal fixation. According to some embodiments, the head 30 may include at least part of the outer member engagement part 25.

The outer member shaft 26 is generally elongate in shape, and has a substantially linear axis. In some embodiments, the outer member shaft 26 is substantially cylindrical in shape. In other embodiments, the outer member shaft 26 may have a cross section other than circular.

The outer member cannula 28 is generally elongate in shape, and has a substantially linear axis. In some embodiments, the outer member cannula 28 is substantially cylindrical in shape. In other embodiments, the outer member cannula 28 may have a cross section other than circular. According to various embodiments, the outer member cannula 28 has an outer member cannula surface 29 that is free of protrusions that would restrict relative axial movement and/or relative radial movement between the inner member 10 and the outer member 20 when the two-part screw 1 is not in final alignment. In exemplary embodiments, the outer member cannula surface 29 is threadless. Alternatively, the inner member shaft (e.g., 16) and the outer member cannula surface 29 may be threaded to receive one another. The threading may extend the entire length of the inner member shaft and the outer member cannula surface 29 or less than the entire extent.

Figure 5:
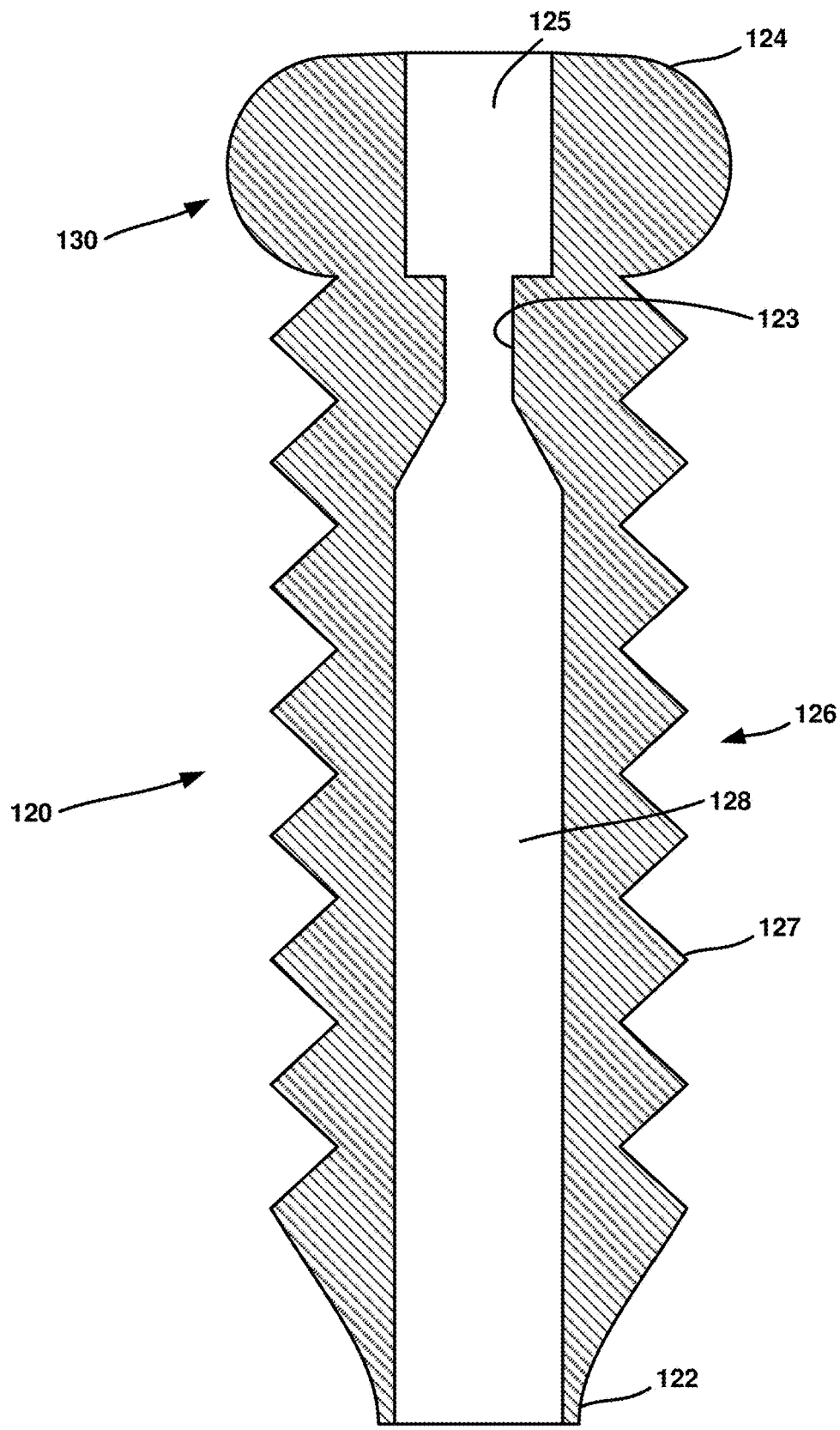
FIG. 5 is a cross-sectional view of another outer member according to various embodiments.

In some embodiments, as shown in FIG. 3, the entire length of the outer member cannula 28 is consistent in diameter. In other embodiments, as shown in FIG. 5, the outer member cannula 128 has a portion having a smaller diameter than the rest of the outer member cannula 128.

In some embodiments, the outer member cannula 28 may extend through the entirety of the outer member 20 including the head 30. This allows an inner member driver (e.g., 40 as shown in FIG. 6) to extend through the outer member 20 to reach the inner member 10.

The dimensions of the outer member 20 may be at least partly determined by the type of application. In some embodiments, the length of the outer member 20 may be determined based on the size of the pedicle.

In some embodiments, the diameter of the outer member cannula 28 ranges from about 8 gauge to about 14 gauge, from about 9 gauge to about 12 gauge, from about 10 gauge to about 12 gauge, or from about 9 gauge to about 11 gauge. In some embodiments, the diameter of the outer member cannula 28 ranges from about 2 mm to about 4 mm, from about 2.1 mm to about 3.9 mm, from about 2.2 mm to about 3.8 mm, from about 2.3 mm to about 3.7 mm, from about 2.4 mm to about 3.6 mm, from about 2.5 mm to about 3.5 mm, from about 2.6 mm to about 3.4 mm, from about 2.7 mm to about 3.3 mm, or from about 2.8 mm to about 3.2 mm. In exemplary embodiments, the diameter of the outer member cannula 28 is about 11 gauge. In exemplary embodiments, the diameter of the outer member cannula 28 is about 3 mm.

In some embodiments, the length of the outer member 20 ranges from about 10 mm to about 70 mm, from about 15 mm to about 65 mm, from about 20 mm to about 60 mm, from about 25 mm to about 55 mm, from about 30 mm to about 55 mm or from about 35 mm to about 60 mm. In exemplary embodiments, the length of the outer member 20 is about 40 mm. In some embodiments, the length of the outer member 20 ranges from about 30 mm to about 35 mm, from about 35 mm to about 40 mm, from about 40 mm to about 45 mm, from about 45 mm to about 50 mm, from about 50 mm to about 55 mm or from about 55 mm to about 60 mm. In exemplary embodiments, the length of the outer member 20 is about 40 mm Relationship Between Inner Member and Outer Member The inner member 10 may be configured to fit within the outer member cannula 28. In some embodiments, the inner member 10 may substantially fill the outer member cannula 28 in at least the region of the outer member shaft 26, such that the two-part screw 1 is a substantially solid implant when the two-part screw 1 is in final alignment. This may allow for improved or optimal strength without any significant points of weakness in the two-part screw 1 in final alignment. In some embodiments, as shown in FIG. 1B, the inner member tip 11 may protrude from the outer member distal end 22 when the two-part screw 1 is in final alignment.

In some embodiments, as shown in FIGS. 1A and 1B, the inner member 10 and the outer member 20 may be coaxial.

The inner member 10 may further include an inner member interference fit portion 13 configured to interact with an outer member interference fit portion 23 of the outer member 20 to form an interference fit between the inner member 10 and the outer member 20 when the two-part screw 1 is in final alignment. In some embodiments, the interference fit restricts or prevents relative axial movement between the inner member 10 and the outer member 20. In some embodiments, the interference fit restricts, prevents or eliminates relative radial movement between the inner member 10 and the outer member 20. In some embodiments, the interference fit does not restrict relative radial movement between the inner member 10 and the outer member 20. Nonlimiting examples of types of interference fit include friction fit, snap fit, or press fit.

As shown in FIGS. 1A-2B, the inner member interference fit portion 13 in various embodiments is at the inner member distal end 12, and has a diameter larger than that of the inner member shaft 16. As shown in FIG. 1B, the inner member interference fit portion 13 presses against a distal end of the outer member cannula 28 (i.e., the outer member interference fit portion 23) to form an interference fit when the two-part screw 1 is in final alignment. As shown in FIG. 1B, when the outer member interference fit portion 23 is advanced over the inner member interference fit portion 13, a local deformation occurs at the outer member interference fit portion 23 and/or the inner member interference fit portion 13, which introduces a zone of high friction between the inner member 10 and the outer member 20. In some embodiments, the interference fit portion 13 may not only be wider than a distal end of the cannula 28 of the inner member 10, but may also have threading intended to cut into the walls of the outer member interference fit portion 23 when retracted into the final alignment, thus creating a high friction that resists further movement between the inner and outer members 10, 20.

In a further aspect, the inner member 10 and the outer member 20 in final alignment may be advanced further into the bone or be withdrawn from the bone as a single unit by applying a rotational force or a counter-rotational force, respectively, to the outer member 20.

In some embodiments, the interference fit between the inner member 10 and the outer member 20 is irreversible. This allows the two-part screw 1 to be handled as a single unit after the interference fit has been made in the final alignment. In other embodiments, the interference fit between the inner member 10 and the outer member 20 is reversible. This allows the two-part screw 1 to be disassembled, such that the inner member 10 and the outer member 20 may be separated and handled separately after the interference fit has been made in the final alignment.

In a further aspect, the interference fit serves to lock the inner member 10 and the outer member 20 in relative axial position once the surgery is complete. The interference fit prevents separation of the inner member 10 and the outer member 20 from relative axial movement due to forces exerted upon the implanted two-part screw 1 during movement of the body.

In some embodiments, the interference fit allows the two-part screw 1 to be removed as a unit during a revision procedure.

The inner member 10 and the outer member 20 may be made of any biocompatible material, providing the material has sufficient strength properties for use in the desired application. Non-limiting examples of materials include titanium, cobalt chrome, or stainless steel. In some embodiments, the inner member 10 and the outer member 20 are formed from a same or similar material. In other embodiments, the inner member 10 and the outer member 20 are formed from different materials.

FIG. 4 is a diagram illustrating an inner member according to another embodiment. As shown in FIG. 4, inner member 110 includes an inner member tip 111, an inner member distal end 112, an inner member proximal end 114, and an inner member shaft 116. Inner member 110 may include other features as described for inner member 10 shown in FIG. 2.

FIG. 5 is a diagram illustrating an outer member according to another embodiment. As shown in FIG. 5, outer member 120 includes an outer member distal end 122, an outer member proximal end 124, an outer member shaft 126, and an outer member cannula 128. Outer member 120 may include other features as described for outer member 20 shown in FIG. 3, such as the outer member engagement part 125. In some embodiments, the outer member 120 may include a head 130. Also, the outer member outer surface 127 may include at least one threaded portion for advancing the outer member 120 into bone when rotational force is applied to the outer member 120, and also for anchoring the outer member 120 into bone.

As shown in FIG. 4, inner member 110 may include an inner member interference fit portion 113 at the inner member proximal end 114. As shown in FIG. 5, outer member 120 may include an outer member interference fit portion 123 near the outer member proximal end 124. In various embodiments, the outer member interference fit portion 123 is a portion of the outer member cannula 128 that has a smaller inner diameter than that of the rest of the outer member cannula 128. When the inner member 110 is moved axially within the outer member cannula 128, toward the out member proximal end 124, the outer member interference fit portion 123 presses against the inner member interference fit portion 113 of the inner member 110 to form an interference fit.

In other embodiments, the inner member may have more than one interference fit portion, and the outer member may have more than one interference fit portion. The two-part screw when in final alignment may have an interference fit in more than one location.

Surgical Assembly

FIG. 6 is a diagram illustrating a surgical assembly according to various embodiments. As shown in FIG. 6, a surgical assembly 5 includes a two-part screw 1, an inner member driver 40, and an outer member driver 50.

Inner Member Driver

The inner member driver 40 includes an inner member driver distal end 42, an inner member driver proximal end 44, an inner member driver shaft 46, and an inner member driver handle 48 located at the inner member driver proximal end 44, as shown in FIG. 6.

The inner member driver 40 has an inner member driver engagement part 45 at the inner member driver distal end 42 for engagement with the inner member engagement part 15 at the inner member proximal end 12. In some embodiments, the inner member 10 and the inner member driver 40 have an engagement that restricts relative axial movement between the inner member 10 and the inner member driver 40. In some embodiments, the inner member 10 and the inner member driver 40 have an engagement that restricts relative radial movement between the inner member 10 and the inner member driver 40. Non-limiting examples of an engagement between the inner member engagement part 15 and the inner member driver engagement part 45 include a friction fit, a snap fit, a press fit, an interference fit, a bayonet fit, a threaded fit, or an adhesion.

In some embodiments, the inner member 10 and at least the inner member driver distal end 42 are integrally formed, and the inner member 10 is separated from the inner member driver distal end 42 after being implanted by breaking the integrally formed unit. In some embodiments, the integrally formed inner member 10 and at least the inner member driver distal end 42 are separated at a designated breaking point, for example a score mark.

In a further aspect, the inner member 10 is capable of advancing into bone when axial force is applied to the inner member 10. In some embodiments, an axial force is applied to the inner member driver handle 48, and the axial force is transferred through the inner member driver shaft 46 and the inner member driver distal end 42 to the inner member 10 by the engagement between the inner member driver engagement part 45 and the inner member engagement part 15. In some embodiments, an axial force is applied to the inner member driver handle 48 by striking an inner member driver handle top surface 47 with a tool, for example a hammer or mallet.

Outer Member Driver

As also shown in FIG. 6, the outer member driver 50 includes an outer member driver distal end 52, an outer member driver proximal end 54, an outer member driver shaft 56, and an outer member driver handle 58 located at the outer member driver proximal end 54.

The outer member driver 50 has an outer member driver engagement part 55 at the outer member driver distal end 52 for engagement with the outer member engagement part 25 at the outer member proximal end 24. In some embodiments, the outer member 20 and the outer member driver 50 have an engagement that restricts relative radial movement between the outer member 20 and the outer member driver 50. In some embodiments, the outer member 20 and the outer member driver 50 have an engagement that restricts relative axial movement between the outer member 20 and the outer member driver 50. Non-limiting examples of an engagement between the outer member engagement part 25 and the outer member driver engagement part 55 include a friction fit, a snap fit, a press fit, an interference fit, a bayonet fit, a counter-threaded fit, or an adhesion.

In a further aspect, the outer member 20 is capable of advancing into bone when force is applied to the outer member 20. In a further aspect, the outer member 20 is capable of advancing into bone when rotational force is applied to the outer member 20. In some embodiments, a rotational force is applied to the outer member driver handle 58, and the rotational force is transferred through the outer member driver shaft 56 and the outer member driver distal end 52 to the outer member 20 by the engagement between the outer member driver engagement part 55 and the outer member engagement part 25. Similarly, the outer member 20 is capable of withdrawing from the bone when counter-rotational force is applied to the outer member driver handle 58, and the counter-rotational force is transferred through the outer member driver shaft 56 and the outer member driver distal end 52 to the outer member 20 by the engagement between the outer member driver engagement part 55 and the outer member engagement part 25.

The outer member driver 50 has an outer member driver shaft 56 that is cannulated and configured to accept the inner member driver shaft 46 within the cannula 59. According to various embodiments, the inner member driver shaft 46 and the cannula 59 of the outer member driver shaft 56 are free of protrusions that would restrict relative axial movement and/or relative radial movement between the inner member driver 40 and the outer member driver 50.

The inner member driver 40 and the outer member driver 50 may be made of any suitable material, providing the material has sufficient strength properties for use in the desired application. Nonlimiting examples of materials include titanium, cobalt chrome, or stainless steel. In some embodiments, the inner member driver 40 and the outer member driver 50 are formed from a same or similar material. In other embodiments, the inner member driver 40 and the outer member driver 50 are formed from different materials. In some embodiments, at least the inner member driver distal end 42 is made from the same material as the inner member proximal end 14.

Procedure for Using Surgical Assembly

When assembled, as shown in FIG. 6, the surgical assembly includes the inner member 10, the outer member 20, the inner member driver 40, and the outer member driver 50. The inner member driver engagement part 45 is engaged with the inner member engagement part 15. The outer member driver engagement part 55 is engaged with the outer member engagement part 25. The inner member driver shaft 46 extends through the outer member driver shaft 56 and at least partly into the outer member cannula 28. The inner member 10 is partially within the outer member cannula 28. The outer member driver handle 58 is distal to the inner member driver handle 48.

In a further aspect, a portion of the inner member distal end 12', such as the inner member tip 11, protrudes from the outer member distal end in the surgical assembly 5, such that the inner member distal end 12 may contact the bone before any portion of the outer member 20 contacts the bone. In a further aspect, the length of inner member 10 protruding from the outer member 20 may be adjustable. In a further aspect, the length of inner member 10 protruding from the outer member 20 may be temporarily fixed. In a further aspect, the length of inner member 10 protruding from the outer member 20 may be determined by the relative position of the inner member driver 40 and the outer member driver 50.

As shown in FIG. 6, the inner member 10 protrudes from the outer member distal end 22 by a length L. In some embodiments, the length L is set by the abutment of an inner member driver handle bottom surface 49 against an outer member driver handle top surface 57. According to various embodiments, the length L is set to prevent the inner member 10 from advancing too far, for example to prevent the inner member 10 from advancing completely through the bone.

In some embodiments, the length L may be adjusted by changing the relative position of at least the inner member driver handle bottom surface 49 with respect to the inner member driver engagement part 45. According to various embodiments, this may be accomplished by having an inner member driver handle 48 that is variable in height, or by having an inner member driver handle 48 that may move in an axial direction along the inner member driver shaft 46. In the latter case, at least a portion of the inner member driver shaft 46 would protrude through the inner member driver handle 48.

In some embodiments, the length L may be adjusted by changing the relative position of at least the outer member driver handle top surface 57 with respect to the outer member driver engagement part 55. According to various embodiments, this may be accomplished by having an outer member driver handle 58 that is variable in height, or by having an outer member driver handle 58 that may move in an axial direction along the outer member driver shaft 56. In the latter case, at least a portion the outer member driver shaft 56 would protrude through the inner member driver handle 48.

According to various embodiments, the inner member driver 40 and/or the outer member driver 50 include markings to assist in setting the length L.

In a further aspect, the surgical assembly 5 is advanced toward the bone by applying an axial force to the inner member driver 40. The inner member 10 penetrates the bone. In some embodiments, advancement of the inner member 10 into the bone is guided with the assistance of various imaging techniques.

According to exemplary embodiments, axial force applied to the inner member driver handle top surface 47 is transferred to the inner member 10 as described above. Simultaneously, the inner member driver handle bottom surface 49 transfers the axial force to the outer member driver handle top surface 57, and the axial force is transferred to the outer member 20 by the engagement between the outer member driver engagement part 55 and the outer member engagement part 25. The entire surgical assembly 5 thus advances as a unit when axial force is applied to the inner member driver handle top surface 47.

In some embodiments, the inner member driver 40, the outer member driver 50, the inner member 10, and/or the outer member 20 include depth markings to gauge how far the surgical assembly 5 is advanced toward the bone.

In a further aspect, the advancement of the surgical assembly 5 toward the bone is halted by the abutment of the outer member distal end 22 against the surface of the bone. In some embodiments, the inner member driver 40 is separated from the inner member 10 at this point. In other embodiments, the inner member driver 40 is separated from the inner member 10 at a later point in the procedure. To separate the inner member driver 40, the engagement between the inner member driver engagement part 45 and the inner member engagement part 15 is broken, and the inner member driver 40 is removed.

In a further aspect, the outer member 20 is advanced into the bone by applying a rotational force to the outer member driver 50. In some embodiments, rotational force applied to the outer member driver handle 58 is transferred to the outer member 20 as described above. According to exemplary embodiments, the rotational force applied to the outer member driver 50 is not transferred to the inner member 10. In some embodiments, rotational force applied to the outer member driver 50 is not transferred to the inner member driver 40.

In a further aspect, the outer surface of the inner member 10 and/or the outer member cannula surface 29 are configured such that relative axial movement between the inner member 10 and the outer member 20 is not restricted until the inner member 10 and the outer member 20 are in a final alignment. In a further aspect, the outer surface of the inner member 10 and/or the outer member cannula surface 29 are configured such that relative radial movement between the inner member 10 and the outer member 20 is not restricted. According to various embodiments, a slip fit exists between the inner member 10 and the outer member cannula 28. In some embodiments, the inner member 10 and the outer member cannula surface 29 are both threadless, which eliminates the potential for cross-threading when the outer member 20 is advanced over the inner member 10.

According to various embodiments, if the inner member driver 40 is held steady or with some retrograde force, and the outer member driver 50 may be turned with an antero-grade force, the outer member 20 will advance over the inner member 10 without advance the inner member 10 any further.

In some embodiments, advancement of the outer member 20 into the bone advances the outer member 20 over the inner member 10 such that the length L decreases. The trajectory of the outer member 20 is determined by the position of the inner member 10 in the bone. The inner member 10 thus acts as a guide for the outer member 20 to ensure that the outer member 20 is implanted in the correct location within the bone.

In a final alignment, the inner member 10 substantially fills the outer member cannula 28 at least in the region of the outer member shaft 26, and an interference fit is formed between the inner member interference fit portion 13 and the outer member interference fit portion 23. When the two-part screw 1 is in final alignment, the inner member 10 and the outer member 20 may be advanced together into the bone by rotational force applied to the outer member driver.

In some embodiments, the final alignment occurs before the two-part screw 1 is in its final position. In this case, the initial trajectory of the outer member 20 as determined by the position of the inner member 10 in the bone is sufficient to ensure that the outer member 20 is implanted in the correct location within the bone.

In some embodiments, the advancement of the outer member 20 into the bone is halted by the abutment of the head 30 against the surface of the bone. In some embodiments, the final alignment occurs before the head 30 abuts against the surface of the bone, as discussed above. In other embodiments, the length L is set such that the final alignment occurs when the head 30 abuts against the surface of the bone.

When the two-part screw 1 is fully implanted into the bone, the engagement between the outer member driver engagement part 55 and the outer member engagement part 25 is broken, and the outer member driver is removed. In some embodiments, the inner member driver 40 and the outer member driver 50 are both removed when the two-part screw 1 is fully implanted into the bone. In other embodiments, the inner member driver 40 and the outer member driver 50 are removed from the surgical assembly 5 at different times.

Surgical Assembly Kit

In a further aspect, a surgical assembly kit may be provided as a modular system with various types and/or sizes of inner members 10, outer members 20, heads 30, inner member drivers 40, and/or outer member drivers 50. Such a kit allows a surgeon to choose types and/or sizes of components to form a surgical assembly 5 that is suitable for a particular need.

Figure 7:
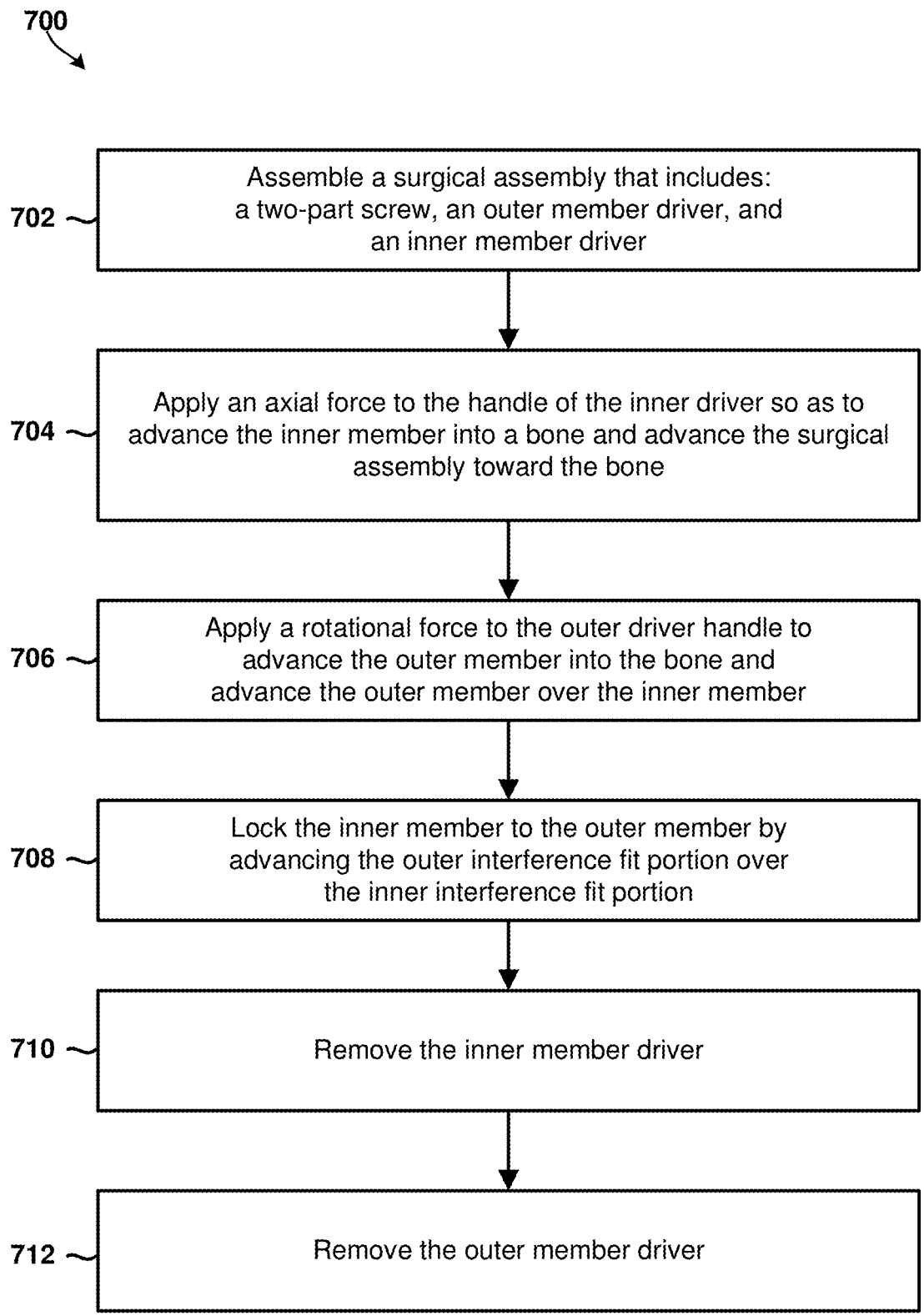
FIG. 7 is a process flow diagram illustrating a method of using a surgical assembly according to various embodiments.

FIG. 7 illustrates a method 700 of treating a subject by implanting a bone screw in accordance with the various embodiments. In operation block 702, a user (e.g., surgeon, specialist, technician, machine, etc.) may assemble the components of a surgical assembly that includes a two-part screw (or bone screw), an outer member driver, and an inner member driver.

The two-part screw of the surgical assembly may include an outer member and an inner member. The outer member may include a distal end, a proximal end having an outer member engagement part, a cannula, and at least one outer member interference fit portion. The inner member may include a distal end, a proximal end having an inner member engagement part, and at least one inner member interference fit portion. The inner member may be partially within the cannula of the outer member. The inner member may be unrestricted in axial and/or radial movement within the cannula of the outer member. In some embodiments, the inner member interference fit portion and the outer member interference fit portion may be configured to form an interference fit between the inner member and the outer member when the inner member is substantially within the cannula of the outer member.

The outer member driver of the surgical assembly may include an outer driver handle, a cannulated outer driver shaft, and an outer driver proximal end having an outer driver engagement part in fixed rotational engagement with the outer member engagement part.

The inner member driver of the surgical assembly may include an inner driver handle proximal to the outer driver handle, an inner driver shaft within the cannulated outer driver shaft, and an inner driver proximal end having an inner driver engagement part in fixed axial engagement the inner member engagement part.

Returning to FIG. 7, in operation block 704, the user (e.g., surgeon, etc.) may apply an axial force to the inner driver handle to advance the inner member into the bone and advance the surgical assembly toward the bone. In some embodiments, this may be accomplishing by striking the inner driver handle with a hammer or tool. In operation block 706, the user may apply a rotational force to the outer driver handle to advance the outer member into the bone and advance the outer member over the inner member. In operation block 708, the user may lock the inner member to the outer member by advancing the at least one outer interference fit portion over the at least one inner interference fit portion. In operation block 710, the user may remove the inner member driver. In operation block 712, the user may remove the outer member driver.

In some embodiments, method 700 may further include using an imaging technique to image the trajectory and location of the inner member before, during, and/or after applying axial force to the inner driver handle in operation block 704.

Figure 8A:
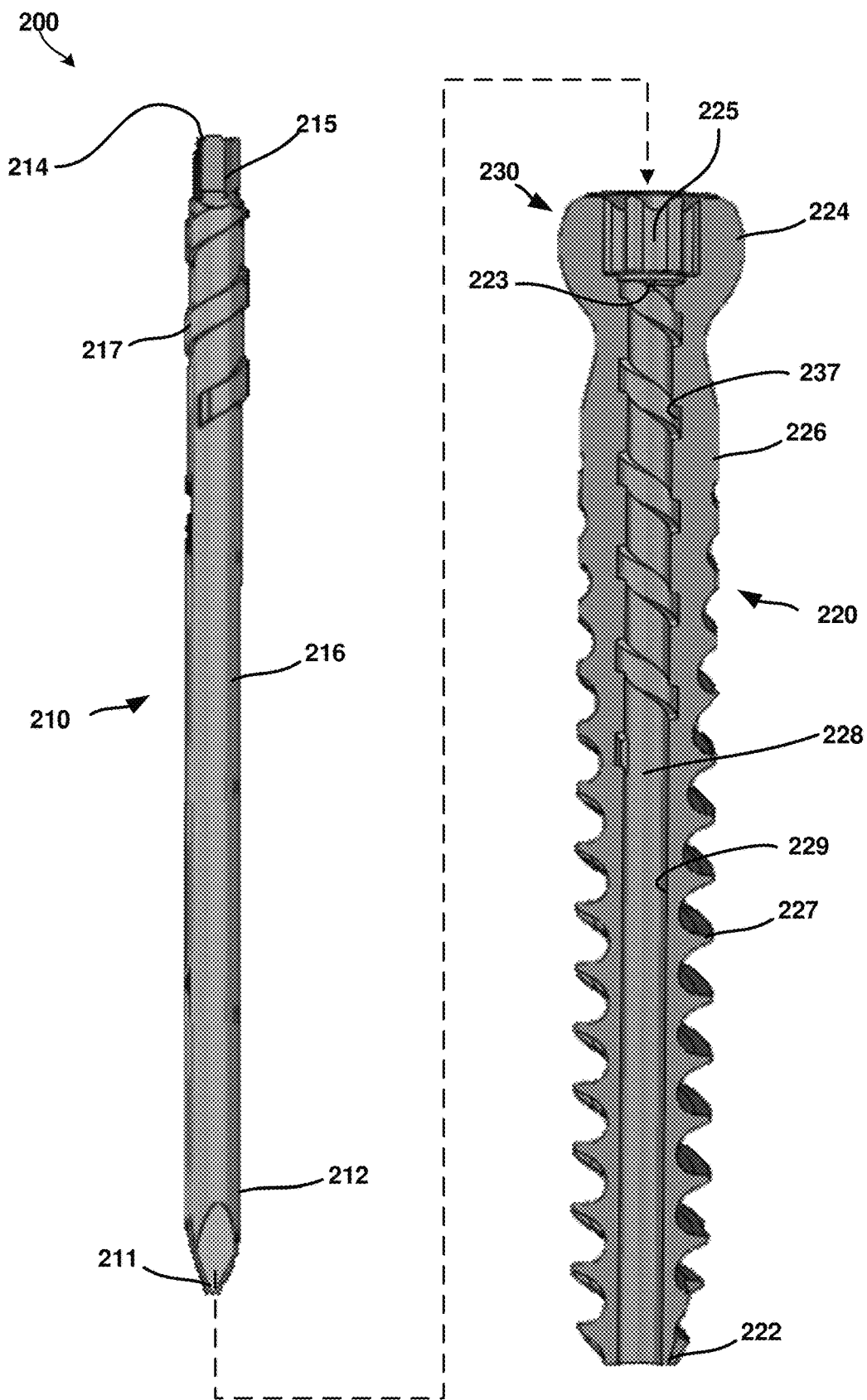
FIG. 8A is a cross-sectional view of a two-part screw prior to assembly according to various embodiments.
Figures 8B, 8C, 8D:
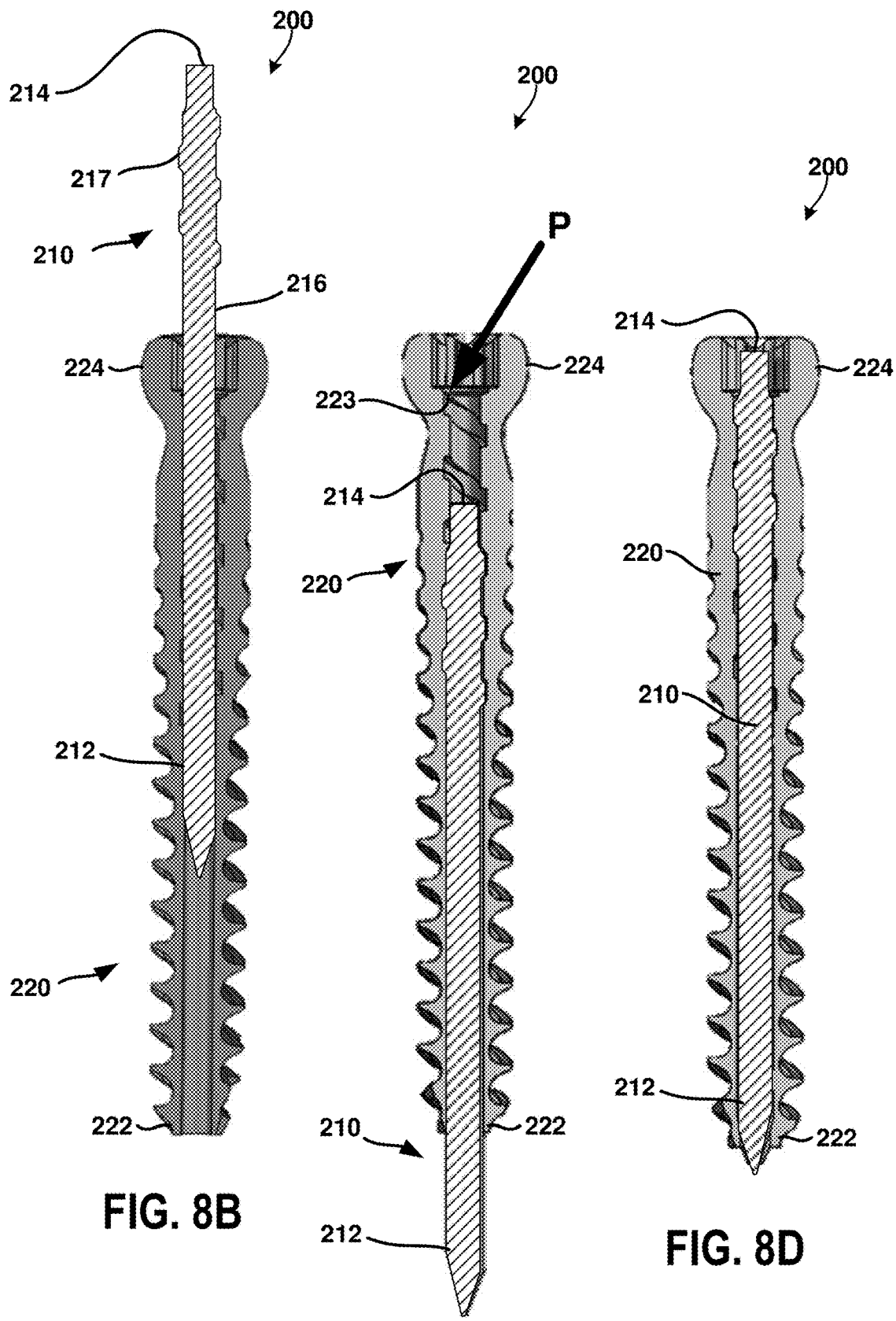
FIGS. 8B-8D are cross-sectional views of the two-part screw of FIG. 8A in various stages of assembly according to various embodiments.

FIGS. 8A-8D are diagrams illustrating a cross-sectional view of an inner member 210 and an outer member 220 of a two-part screw in various stages of assembly. FIG. 8A illustrates the two-part screw prior to 200 prior to assembly, such that the inner member 210 has not yet been inserted into the outer member 220. FIG. 8B illustrates the two-part screw 200 at an early stage of assembly, where the inner member 210 has been inserted half way into the outer member cannula 228 from an outer member proximal end 224. FIG. 8C illustrates the two-part screw 200 in a deployed position that includes a significant portion of the inner member distal end 212 protruding from the outer member distal end 222. In the deployed position (i.e., illustrated in FIG. 8C) a surgeon, technician, or other user may punch P an outer member interference fit portion 223, using a separate tool from the outside, which displaces some material of the inner member into an uppermost part of the outer member cannula 228. The displaced material creates a deformation in the uppermost part of the outer member cannula 228 that traps the inner member 210 substantially within the outer member cannula 228. The deformation may be a protrusion extending into the outer member cannula 228, which may block the inner member 210 from retracting very far beyond the outer member interference fit portion 223. FIG. 8D illustrates the two-part screw 200 in a retracted position in which the inner member 210 has been fully retracted from the deployed position. In the retracted position, an upper part of the inner member 210 may abut the displaced material, which blocks the inner member 210 from backing out of the outer member 220. In particular, an uppermost end of the outer threading 217 of the inner member 210 may engage the displaced material protruding into an inner threading 237 of the outer member 220, which prevent further axial movement of the inner member 210 in the proximal direction relative to the outer member 220.

The inner member 210 may include an inner member tip 211, an inner member distal end 212, an inner member proximal end 214, and an inner member shaft 216. The inner member 110 may also include other features as described above with regard to other embodiments of the inner member (e.g., 10, 110). The outer member 220 may include an outer member distal end 222, an outer member proximal end 224, an outer member shaft 226, and an outer member cannula 228.

The inner member 210 may also include an outer threading 217, near the inner member proximal end 214, that is configured to fit into the inner threading 237 of the outer member 220. Also, the inner member 210 may include an inner member engagement part 215 located at the inner member proximal end 214. The inner member engagement part 215 may be a male or female coupling structure. The outer threading 217 may be limited to an upper half or at least an upper portion of the inner member 210. Thus, a lower half or lower portion of the inner member 210 may have a smooth cylindrical surface that is not as wide as the widest part of the outer threading 217. Similarly, the inner threading 237 of the outer member 220 may be limited to an upper half or at least an upper portion of the outer member 220. Thus, a lower cannula portion 229 of the outer member cannula 228 may have a smooth cylindrical surface that is not as wide as the widest part of the inner threading 237. By limiting the threading 217, 237 to only an upper portion of the inner and outer members 210, 220, the inner member 210 may be limited in how far through the outer member 220 it can pass. Also, in this way the outer member cannula 228 may be configured to only receive the inner member 210 therein from the outer member proximal end 224.

The outer member 220 may also include other features as described above with regard to other embodiments of the outer member (e.g., 20, 120), such as the outer member engagement part 225. In some embodiments, the outer member 220 may include a head 230. Also, the outer member outer surface 227 may include at least one threaded portion for advancing the outer member 220 into bone when rotational force is applied to the outer member 220, and also for anchoring the outer member 220 into bone. The threading on the outer member outer surface 227 may be reversed to the outer threading 217 of the inner member 210 in order to prevent the inner member 210 from being driven back into the outer member 220 and out of the bone 500 when the outer member 220 is screwed into the bone 500 (as described below with regard to FIGS. 10A-10C).

Figure 9A:
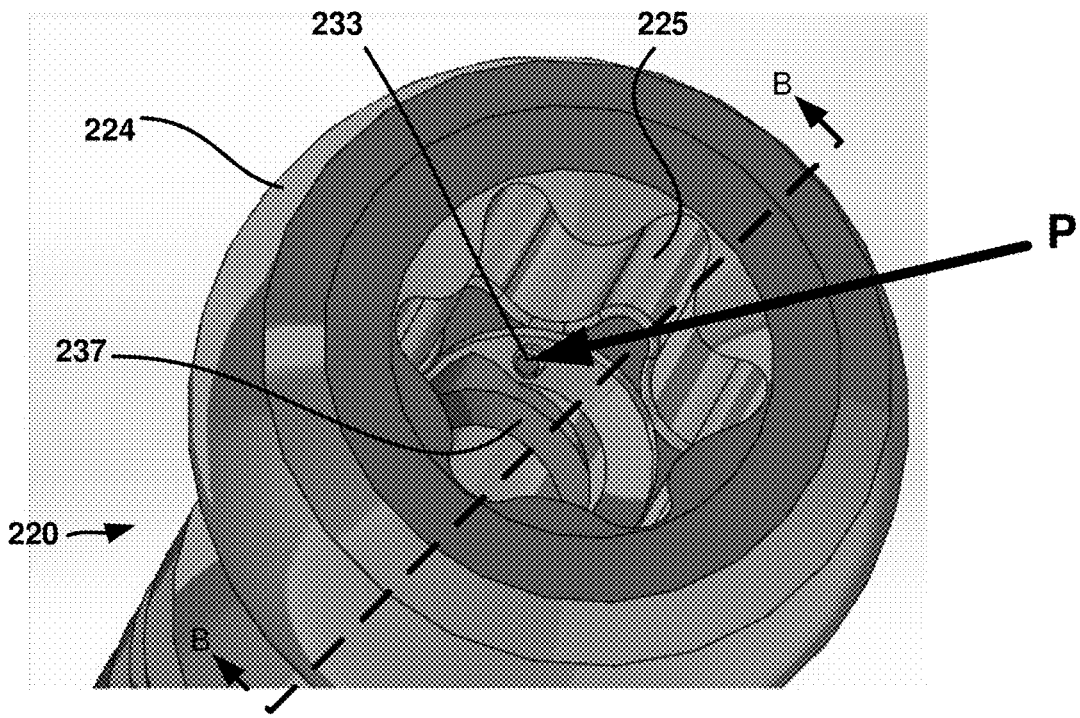
FIG. 9A is a top isometric view of a top portion of an outer member of a two-part screw in accordance with various embodiments.
Figure 9B:
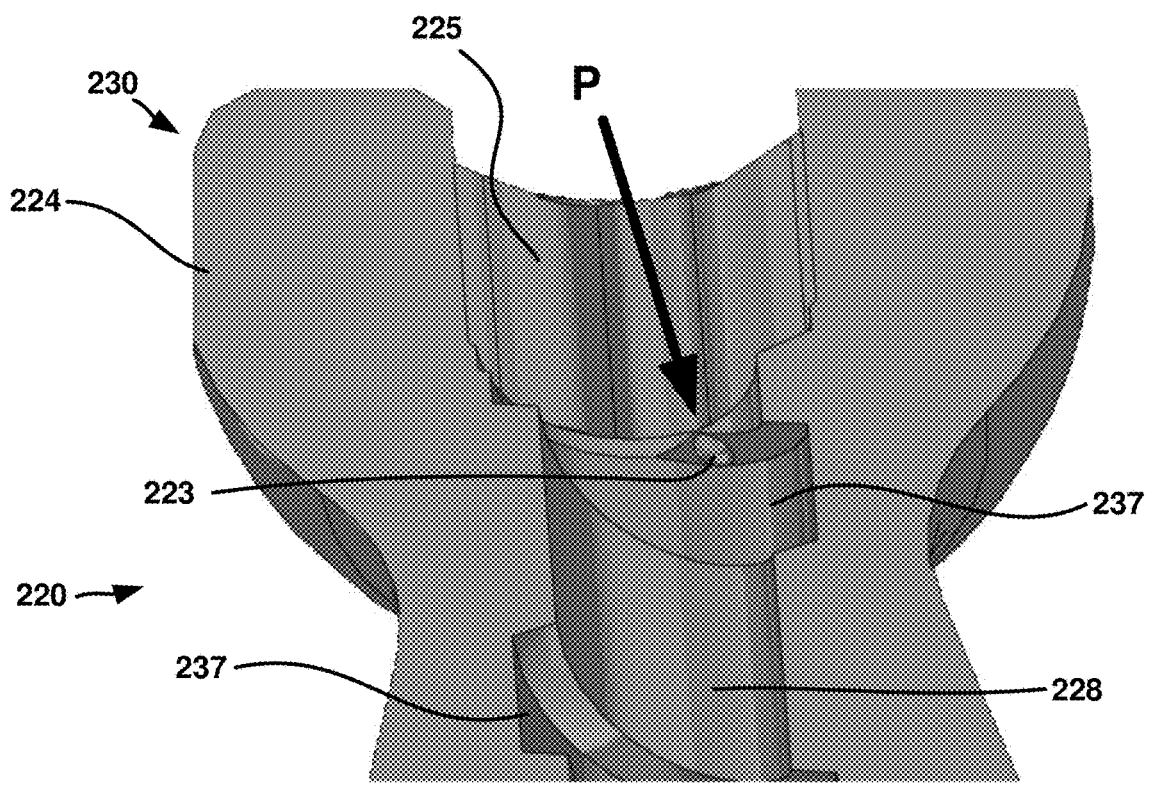
FIG. 9B is a cross-sectional view of the top portion of the outer member in FIG. 9A at section B-B.
Figure 9C:
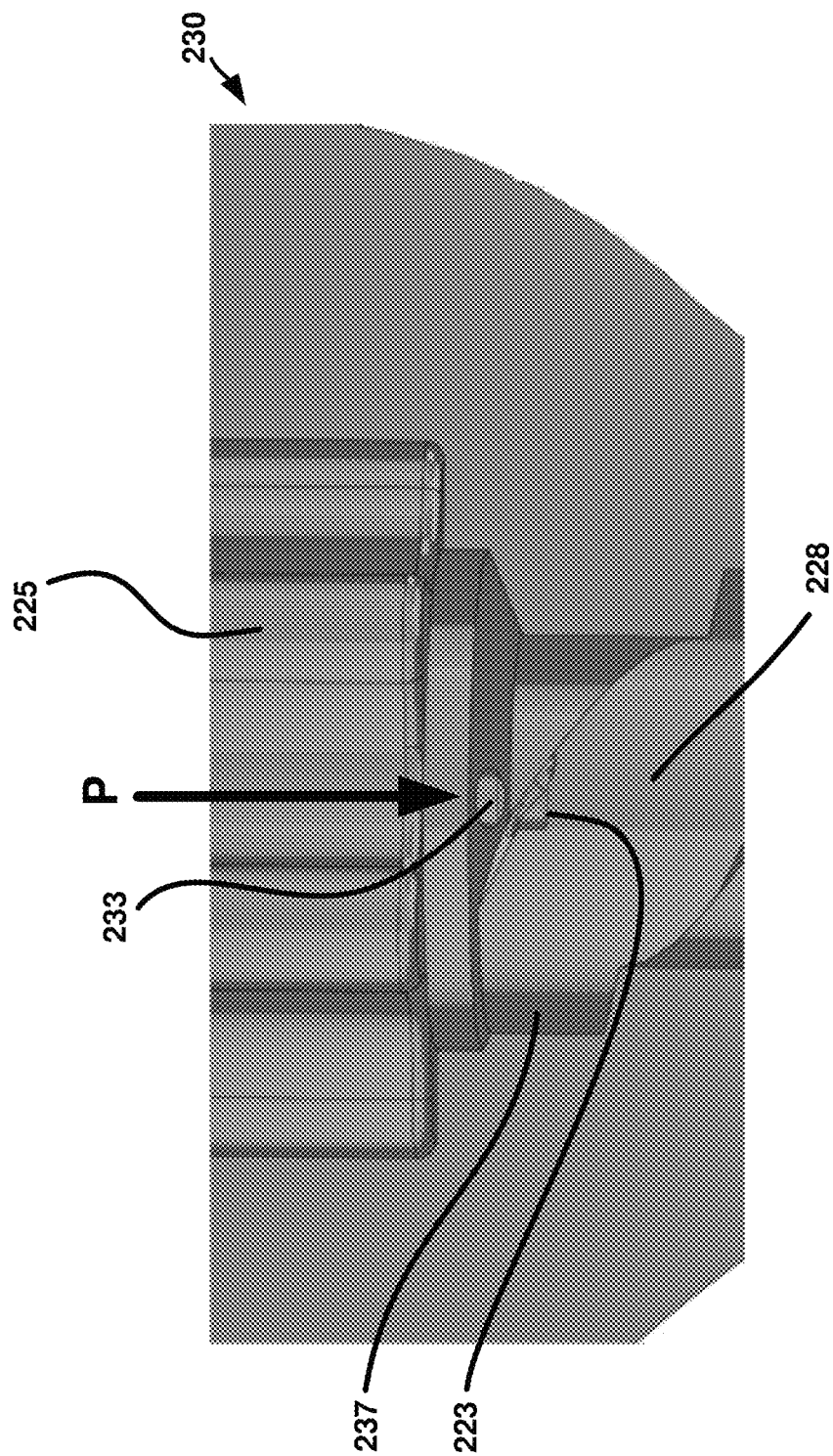
FIG. 9C is a cross-sectional view of a top portion of an outer member of a two-part screw according to various embodiments.

FIGS. 9A-9C illustrate a top portion of the outer member 220 of a two-part screw in accordance with various embodiments. In particular, FIGS. 9A-9C show a relief of the outer member interference fit portion 223, which may be located near a proximal end of the outer member cannula 228. In various embodiments, the outer member interference fit portion 223 may be formed as a deformation in the outer member cannula 228, after the inner member (e.g., 210) is inserted therein. Once the inner member has been inserted into the outer member cannula 228 far enough that the inner member proximal end (e.g., 214) is fully inside the outer member cannula 228, the punch tool P may be used to make a protrusion into the inner threading 237 of the outer member 220. The punch tool P may be inserted into a pilot hole 233 that may tell the surgeon, technician, and/or user where to punch and hold the punch tool P in a proper position. In addition, the pilot hole 233 may form a weak spot in the inner member (e.g., due to the removal of material), making easy to punch and form a deformation inside the outer member cannula 228. The protrusion forms the outer member interference fit portion 223, which traps the inner member 210 substantially within the outer member cannula 228. Once the outer member interference fit portion 223 is formed and the inner member 110 is moved axially within the outer member cannula 128, toward the outer member proximal end 124, the outer threading 217 on the inner member 210 will run into the outer member interference fit portion 223, which will prevent any further axial progress by the inner member 210 toward the outer member proximal end 224.

Figure 10A:
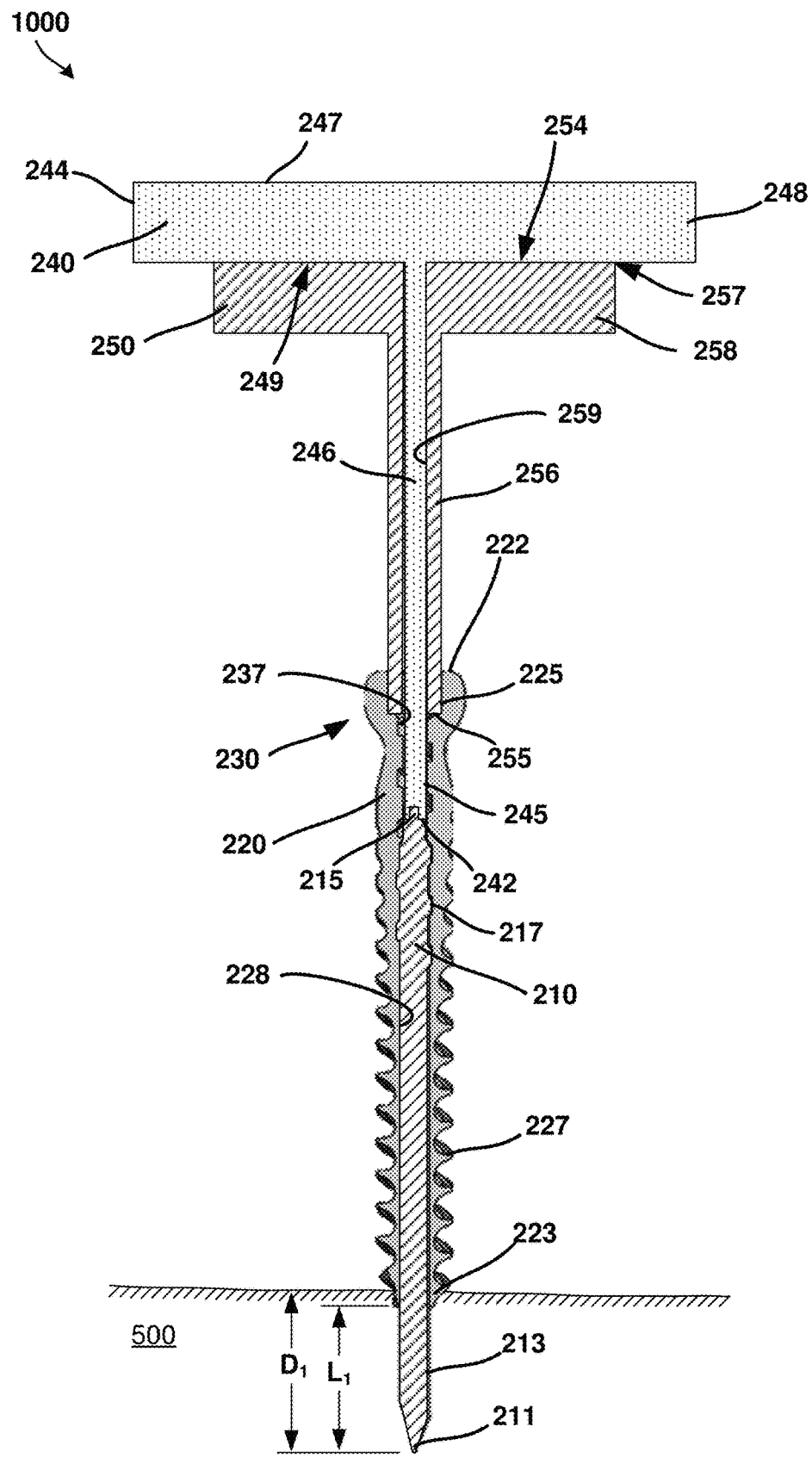
FIGS. 10A-10C are cross-sectional views of a surgical assembly in various stages of implantation in bone according to various embodiments.
Figure 10B:
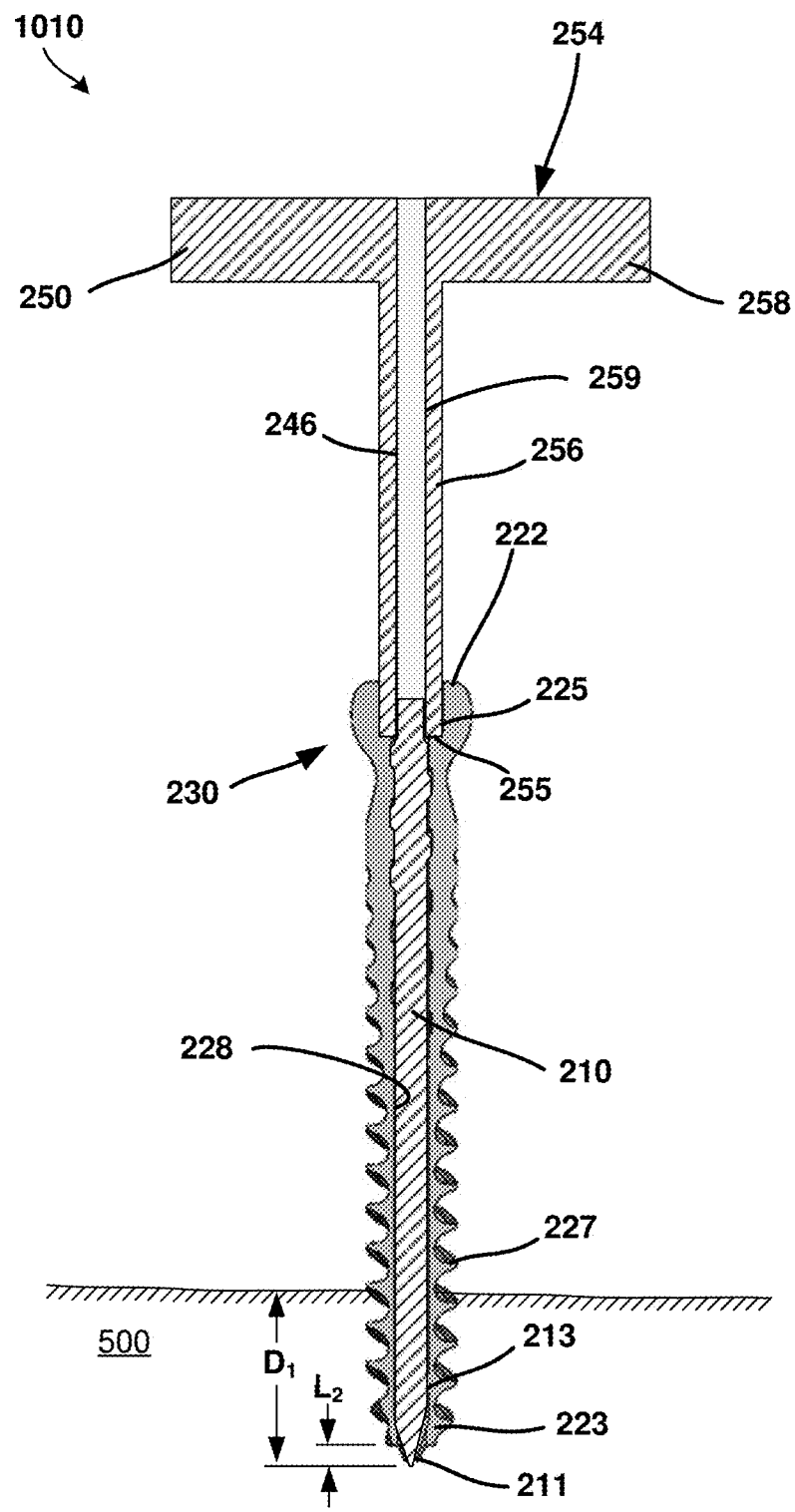
Figure 10C:
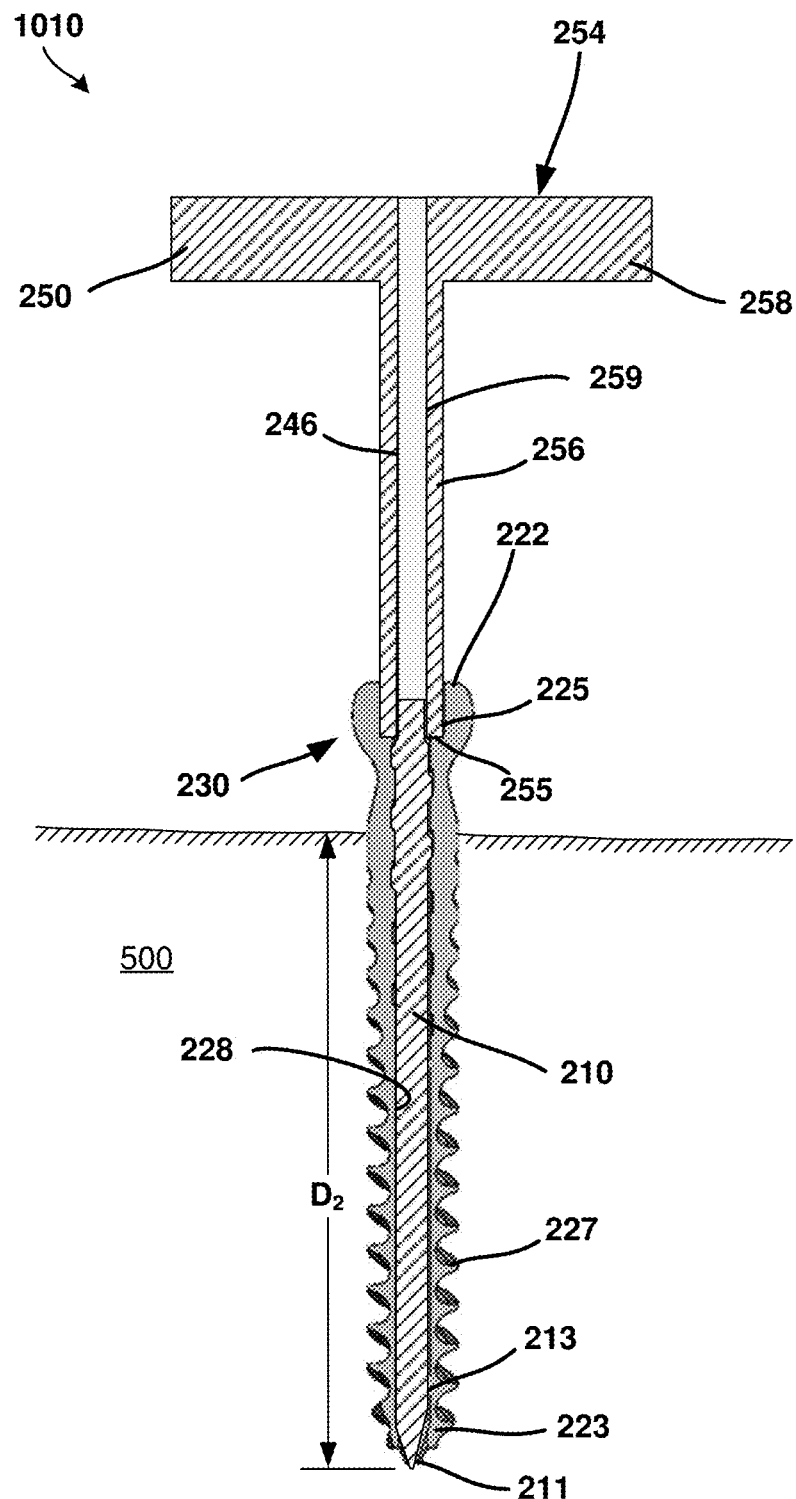
Figure 11:
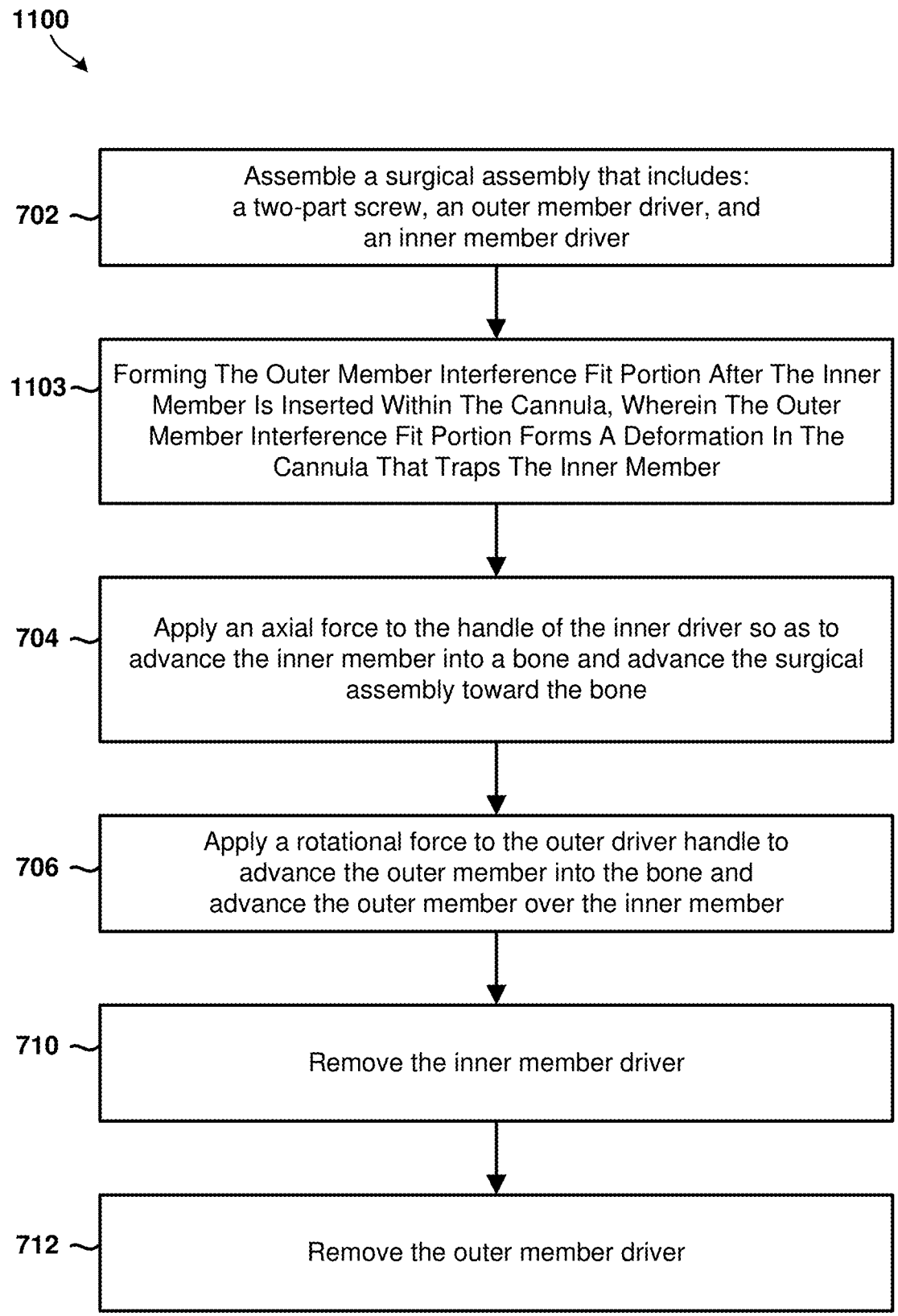
FIG. 11 is a process flow diagram illustrating a method of using a surgical assembly according to various embodiments.

FIGS. 10A-10C illustrate a series of stages of a surgical application of the two-part screw of various embodiments. In particular, FIG. 10A shows a surgical assembly 1000 that includes the inner member 210, the outer member 220, an inner member driver 240, and an outer member driver 250. In FIG. 10A the surgical assembly 1000 is in a deployed position with an inner member tip 211 extended beyond the outer member distal end 223.

To assemble the surgical assembly 1000 a surgeon, technician, or user may insert the inner member 210 into the outer member cannula 228 through the outer member proximal end 222. The inner member 210 should drop down into the outer member cannula 228 until a distal side of the outer threading 217 of the inner member 210 reaches a proximal side of the inner threading 237 of the outer member 220. Thereafter, an outer member driver engagement part 255 may be inserted into the outer member engagement part 225.

In this way, the outer member driver 250 gets mounted on top of the outer member 220 and the inner member 210 is seated partially therein. Thereafter, the inner member driver engagement part 245 may be inserted into a cannula 259 of an inner member driver shaft 246 through a proximal end 254 of an outer member driver handle 258. This will eventually cause an inner member driver engagement part 242 to mate with or engage the inner member engagement part 215 on the inner member proximal end 214. In this way, once the inner member driver engagement part 242 is engaged with the inner member engagement part 215, the inner member driver 240 may be rotated around its longitudinal axis to screw the inner member 210 into the outer member cannula 228 of the outer member 220. The inner member driver 240 may advance the inner member 210 through the outer member cannula 228 until a distal end of the outer threading 217 of the inner member 210 reaches a distal end of the inner threading 237 of the outer member 220, which coincides with a proximal end of the lower cannula portion 229. Thus, once the inner member 210 is fully advanced through the outer member 220, the inner member distal end 213 will extend beyond the outer member distal end 223 a predetermined first length $L_1$. The length that the inner member 210 protrudes from the outer member 220 may be determined by the relative position of the inner member driver 240 and the outer member driver 250. Once an inner member driver handle bottom surface 249 is brought into engagement with an outer member driver handle top surface 257, the surgeon, technician, or user may know the inner member 210 is in the fully deployed position. The maximum length the inner member 210 protrudes from the outer member 220 may be controlled by how long the inner threading 237 of the outer member 220 extend within the outer member cannula 228. The longer the inner threading 237 extend from the outer member proximal end 224, the longer the inner member 210 will protrude from the outer member distal end 222. According to various embodiments, the length $L_1$ may be set to prevent the inner member 210 from advancing too far, for example to prevent the inner member 210 from advancing completely or too far through the bone 500. Additionally, or alternatively, the inner member driver 240 and/or the outer member driver 250 may include markings to assist in setting the length $L_1$.

In some embodiments, the length L1 may be adjusted by changing the relative position of at least the inner member driver handle bottom surface 249 with respect to the inner member driver engagement part 245. According to various embodiments, this may be accomplished by having the inner member driver handle 248 that is variable in height, or by having the inner member driver handle 248 that may move in an axial direction along the inner member driver shaft 246. In the latter case, at least a portion of the inner member driver shaft 246 would protrude through the inner member driver handle 248.

In some embodiments, the length $L_1$ may be adjusted by changing the relative position of at least the outer member driver handle top surface 257 with respect to the outer member driver engagement part 255. According to various embodiments, this may be accomplished by having the outer member driver handle 258 that is variable in height, or by having the outer member driver handle 258 that may move in an axial direction along the outer member driver shaft 256. In the latter case, at least a portion the outer member driver shaft 256 may protrude through the inner member driver handle 248.

In a further aspect, the inner member tip 211, which in the deployed position protrudes from the outer member distal end 223 a length $L_1$, may be placed in contact with bone 500 at a target implantation location. The surgical assembly 1000 may be advanced into the bone 500 by applying an axial force to the inner member driver 240 (e.g., with a hammer or blunt instrument). In some embodiments, advancement of the inner member 210 into the bone 500 may be guided with the assistance of various imaging techniques.

According to exemplary embodiments, axial force applied to the inner member driver handle top surface 247 may be transferred to the inner member 210 as described above. Simultaneously, the inner member driver handle bottom surface 249 transfers the axial force to the outer member driver handle top surface 257, and the axial force is transferred to the outer member 220 by the engagement between the outer member driver engagement part 255 and the outer member engagement part 225. The entire surgical assembly 1000 thus advances as a unit when axial force is applied to the inner member driver handle top surface 247.

In a further aspect, the initial advancement of the surgical assembly 1000 into the bone 500, from the applied axial force, may be halted by the abutment of the outer member distal end 223 against the surface of the bone. In this way, the inner member 210 may be initially driven into the bone 500 an initial depth $D_1$. In some embodiments, the inner member driver 240 may be separated from the inner member 210 at this point. In other embodiments, the inner member driver 240 may be separated from the inner member 210 at a later point in the procedure. To separate the inner member driver 240, the engagement between the inner member driver engagement part 245 and the inner member engagement part 215 may be separated and/or broken, and the inner member driver 240 removed.

FIG. 10B shows a surgical assembly 1010 that includes the inner member 210, the outer member 220, and the outer member driver 250, but the inner member driver (e.g., 240) has been removed. In FIG. 10B, the two-part screw is in a final position, with the inner member 210 retracted within the outer member as far as it will go in the proximal direction, but the surgical assembly 1010 is only in an intermediate position because the two-part screw is not yet fully seated within the bone 500.

In a further aspect, the outer member 220 may be advanced into the bone 500 by applying a rotational force to the outer member driver 250. In some embodiments, rotational force applied to the outer member driver handle 258 is transferred to the outer member 220 as described above. According to exemplary embodiments, the rotational force applied to the outer member driver 250 may not be transferred to the inner member 210. In some embodiments, rotational force applied to the outer member driver 250 may not be transferred to the inner member driver 240.

In a further aspect, the outer surface of the inner member 210 and/or the inner surfaces of the outer member cannula 228 may be configured such that relative axial movement between the inner member 210 and the outer member 220 is not restricted until the inner member 210 and the outer member 220 are in a final alignment. In a further aspect, the outer surface of the inner member 210 and/or the inner surface of the outer member cannula 228 may be configured such that relative radial movement between the inner member 210 and the outer member 220 is not restricted.

In a final alignment, the inner member 210 substantially fills the outer member cannula 228 at least in the region of the outer member shaft 226. In the final alignment, the inner member 210 may still protrude a smaller length $L_2$ from the outer member distal end 223. When the two-part screw is in the final alignment, the inner member 210 and the outer member 220 may be advanced together into the bone 500 by applying a rotational force to the outer member driver 250.

FIG. 10C shows the surgical assembly 1010 still in a final position, with the inner member 210 retracted within the outer member 220 as far as it will go in the proximal direction, but also the surgical assembly 1010 is now further implanted within the bone 500 to a depth $D_2$ that is deeper than the initial depth $D_1$. In some embodiments, the advancement of the outer member 220 into the bone 500 may be halted by the abutment of the head 230 against the surface of the bone 500. In some embodiments, the final alignment occurs before the head 230 abuts against the surface of the bone, as discussed above. In other embodiments, the final depth $D_2$ may be set such that the final alignment occurs when the head 230 abuts against the surface of the bone.

When the two-part screw is fully implanted into the bone 500, the engagement between the outer member driver engagement part 255 and the outer member engagement part 225 may be broken, and the outer member driver 250 may be removed. In some embodiments, the inner member driver 240 and the outer member driver 250 are both removed when the two-part screw is fully implanted into the bone 500. In other embodiments, the inner member driver 240 and the outer member driver 250 are removed from the surgical assemblies 1000, 1010 at different times.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A two-part screw, comprising:
   an inner member comprising a distal end, a proximal end; and
   an outer member comprising a distal end, a proximal end, a cannula, and an outer member interference fit portion,
   wherein the inner member is at least partially disposed within the cannula of the outer member and configured to move axially within the cannula between a deployed position and a retracted position, and
   wherein the outer member interference fit portion is configured to trap the inner member within the cannula of the outer member, wherein the proximal end of the outer member includes a pilot hole configured to receive a punch tool for forming the outer member interference fit portion after the inner member has been loaded into the outer member, wherein in the deployed position a distal portion of the inner member is disposed outside the cannula, wherein in the retracted position at least some of the distal portion is disposed inside the cannula.

2. The two-part screw according to claim 1, wherein the outer member interference fit portion is formed as a deformation in the cannula after the inner member is inserted therein, thereby trapping the inner member within the cannula of the outer member.

3. The two-part screw according to claim 2, wherein the deformation is a protrusion into the cannula configured to engage a proximal portion of the inner member, thereby limiting further movement of the inner member toward the proximal end of the outer member.

4. The two-part screw according to claim 1, wherein the cannula is only configured to receive the inner member therein from the proximal end of the outer member.

5. The two-part screw according to claim 1, wherein the cannula includes an inner threading in the proximal end of the outer member that does not extend to the distal end of the outer member.

6. The two-part screw according to claim 5, wherein the inner member includes an outer threading that is configured to fit into the inner threading of the outer member.

7. The two-part screw according to claim 5, wherein the outer member interference fit portion is formed as a defect in the inner threading that prevents the inner member from moving any further axially toward the proximal end of the outer member once the inner member engages the defect.

8. The two-part screw according to claim 1, wherein a portion of at least one of the inner member and/or the cannula does not include threading.

9. The two-part screw according to claim 1, wherein the outer member comprises an outer member engagement part at the proximal end that is configured to engage with an outer member driver.

10. A surgical assembly comprising:
   at least one two-part screw, comprising:
      an inner member comprising a distal end, a proximal end; and
      an outer member comprising a distal end, a proximal end, a cannula, and an outer member interference fit portion,
      wherein the inner member is at least partially disposed within the cannula of the outer member and configured to move axially within the cannula between a deployed position and a retracted position, and
      wherein the outer member interference fit portion is configured to trap the inner member within the cannula of the outer member, wherein the proximal end of the outer member includes a pilot hole configured to receive a punch tool for forming the outer member interference fit portion after the inner member has been loaded into the outer member, wherein in the deployed position a distal portion of the inner member is disposed outside the cannula, wherein in the retracted position at least some of the distal portion is disposed inside the cannula;
   at least one outer member driver comprising:
      an outer driver handle,
      a cannulated outer driver shaft, and
      an outer driver proximal end comprising an outer driver engagement part in fixed rotational engagement with an outer member engagement part; and
   at least one inner member driver comprising:
      an inner driver handle proximal to the outer driver handle, an inner driver shaft within the cannulated outer driver shaft, and an inner driver proximal end comprising an inner driver engagement part in fixed axial engagement with an inner member engagement part.

11. The surgical assembly according to claim 10, wherein a length of the inner member protrudes from the distal end of the outer member, wherein the length of the inner member that protrudes from the distal end of the outer member is determined by a position of the at least one inner member driver relative to the at least one outer member driver.

12. The surgical assembly according to claim 10, wherein a length of the inner member protrudes from the distal end of the outer member, wherein the length of the inner member that protrudes from the distal end of the outer member is configured to be fixed by positions of the at least one inner member driver and the at least one outer member driver.

13. The surgical assembly according to claim 10, wherein the distal end of the at least one inner member driver is within the cannula of the outer member.

14. The surgical assembly according to claim 10, wherein once the inner member engages the outer member interference fit portion, further rotation of the outer member by the at least one outer member driver rotates the inner member and the outer member in unison.

15. A method of implanting a two-part screw in a bone, the method comprising:
assembling a surgical assembly comprising:
at least one two-part screw, comprising:
an inner member comprising a distal end, a proximal end; and
an outer member comprising a distal end, a proximal end, a cannula,
and an outer member interference fit portion,
wherein the inner member is at least partially disposed within the cannula of the outer member and configured to move axially within the cannula between a deployed position and a retracted position, and
wherein the outer member interference fit portion is configured to trap the inner member within the cannula of the outer member, wherein the proximal end of the outer member includes a pilot hole configured to receive a punch tool for forming the outer member interference fit portion after the inner member has been loaded into the outer member, wherein in the deployed position a distal portion of the inner member is disposed outside the cannula, wherein in the retracted position at least some of the distal portion is disposed inside the cannula;
at least one outer member driver comprising:
an outer driver handle,
a cannulated outer driver shaft, and
an outer driver proximal end comprising an outer driver engagement part in fixed rotational engagement with an outer member engagement part; and
at least one inner member driver comprising:
an inner driver handle proximal to the outer driver handle,
an inner driver shaft within the cannulated outer driver shaft, and
an inner driver proximal end comprising an inner driver engagement part in fixed axial engagement an inner member engagement part;
applying an axial force to the inner driver handle to advance the inner member into the bone and advance the surgical assembly into the bone;
applying a rotational force to the outer driver handle to advance the outer member into the bone and advance the outer member over the inner member;
locking relative rotational movement of the inner member and the outer member by advancing the outer member into the bone until the inner member engages the outer member interference fit portion;
removing the at least one inner member driver; and
removing the at least one outer member driver.

16. The method of claim 15, further comprising:
forming the outer member interference fit portion after the inner member is inserted within the cannula, wherein the outer member interference fit portion forms a deformation in the cannula that traps the inner member.

17. The method of claim 16, wherein the deformation is formed by a protrusion extending into the cannula of the outer member.

18. A surgical assembly kit comprising:
at least one two-part screw, comprising:
an inner member comprising a distal end, a proximal end; and
an outer member comprising a distal end, a proximal end, a cannula, and an outer member interference fit portion,
wherein the inner member is at least partially disposed within the cannula of the outer member and configured to move axially within the cannula between a deployed position and a retracted position, and
wherein the outer member interference fit portion is configured to trap the inner member within the cannula of the outer member, wherein the proximal end of the outer member includes a pilot hole configured to receive a punch tool for forming the outer member interference fit portion after the inner member has been loaded into the outer member, wherein in the deployed position a distal portion of the inner member is disposed outside the cannula, wherein in the retracted position at least some of the distal portion is disposed inside the cannula;
at least one inner member driver comprising:
an inner driver handle,
an inner driver shaft, and
an inner driver proximal end comprising an inner driver engagement part configured to engage an inner member engagement part; and
at least one outer member driver comprising:
an outer driver handle,
a cannulated outer driver shaft configured to accept the inner driver shaft, and
an outer driver proximal end comprising an outer driver engagement part configured to engage an outer member engagement part,
wherein the outer driver handle is configured to be distal to the inner driver handle.

* * * * *